(12) United States Patent
Takei et al.

(10) Patent No.: US 8,542,272 B2
(45) Date of Patent: Sep. 24, 2013

(54) IMAGE GENERATING APPARATUS

(75) Inventors: Shunji Takei, Hachioji (JP); Nobuyuki Doguchi, Hino (JP); Kenji Yamazaki, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 963 days.

(21) Appl. No.: 12/629,394

(22) Filed: Dec. 2, 2009

(65) Prior Publication Data
US 2010/0073731 A1  Mar. 25, 2010

Related U.S. Application Data

(63) Continuation of application No. PCT/JP2008/051908, filed on Feb. 6, 2008.

(30) Foreign Application Priority Data

Jun. 20, 2007 (JP) .................................. 2007-163074

(51) Int. Cl.
*A62B 1/04* (2006.01)
(52) U.S. Cl.
USPC ................... 348/65; 348/45; 348/61; 348/82; 356/241.1; 385/117
(58) Field of Classification Search
USPC ....... 348/65, 45, 61, 82; 356/241.1; 385/117
See application file for complete search history.

(56) References Cited

U.S. PATENT DOCUMENTS

| | | | | |
|---|---|---|---|---|
| 5,507,287 A | * | 4/1996 | Palcic et al. | 600/317 |
| 5,647,368 A | * | 7/1997 | Zeng et al. | 600/476 |
| 5,802,222 A | * | 9/1998 | Rasch et al. | 385/1 |
| 2001/0007921 A1 | | 7/2001 | Hayashi | |
| 2004/0267091 A1 | | 12/2004 | Imaizumi et al. | |
| 2005/0096505 A1 | * | 5/2005 | Imaizumi et al. | 600/180 |
| 2007/0153542 A1 | * | 7/2007 | Gono et al. | 362/574 |
| 2007/0177029 A1 | * | 8/2007 | Wada et al. | 348/222.1 |
| 2008/0259223 A1 | * | 10/2008 | Read et al. | 348/745 |

FOREIGN PATENT DOCUMENTS

| | | |
|---|---|---|
| EP | 1 728 464 A1 | 12/2006 |
| JP | 2001-128927 | 5/2001 |
| JP | 2001-178672 | 7/2001 |

(Continued)

OTHER PUBLICATIONS

International Search Report dated May 13, 2008.

*Primary Examiner* — Andy Rao
*Assistant Examiner* — Shan Elahi
(74) *Attorney, Agent, or Firm* — Scully, Scott, Murphy & Presser, P.C.

(57) ABSTRACT

An image generating apparatus according to the present invention includes: a first light source unit that emits light in a first wavelength band to a subject; a second light source unit that emits light in a second wavelength band, which is a part of the first wavelength band, to the subject; an image pickup unit that picks up an image of the subject and outputs the image as an image pickup signal; a light cut filter unit that cuts light in the second wavelength band reflected from the subject; and a complementary processing unit that applies complementary processing to a component equivalent to the second wavelength band cut by the light cut filter unit in the image of the subject picked up by the image pickup unit in a state in which the subject is illuminated by the light in the first wavelength band.

9 Claims, 13 Drawing Sheets

(56) References Cited

FOREIGN PATENT DOCUMENTS

| JP | 2005-006768 | 1/2005 |
| JP | 2006-166940 | 6/2006 |
| JP | 2006-346196 | 12/2006 |

* cited by examiner

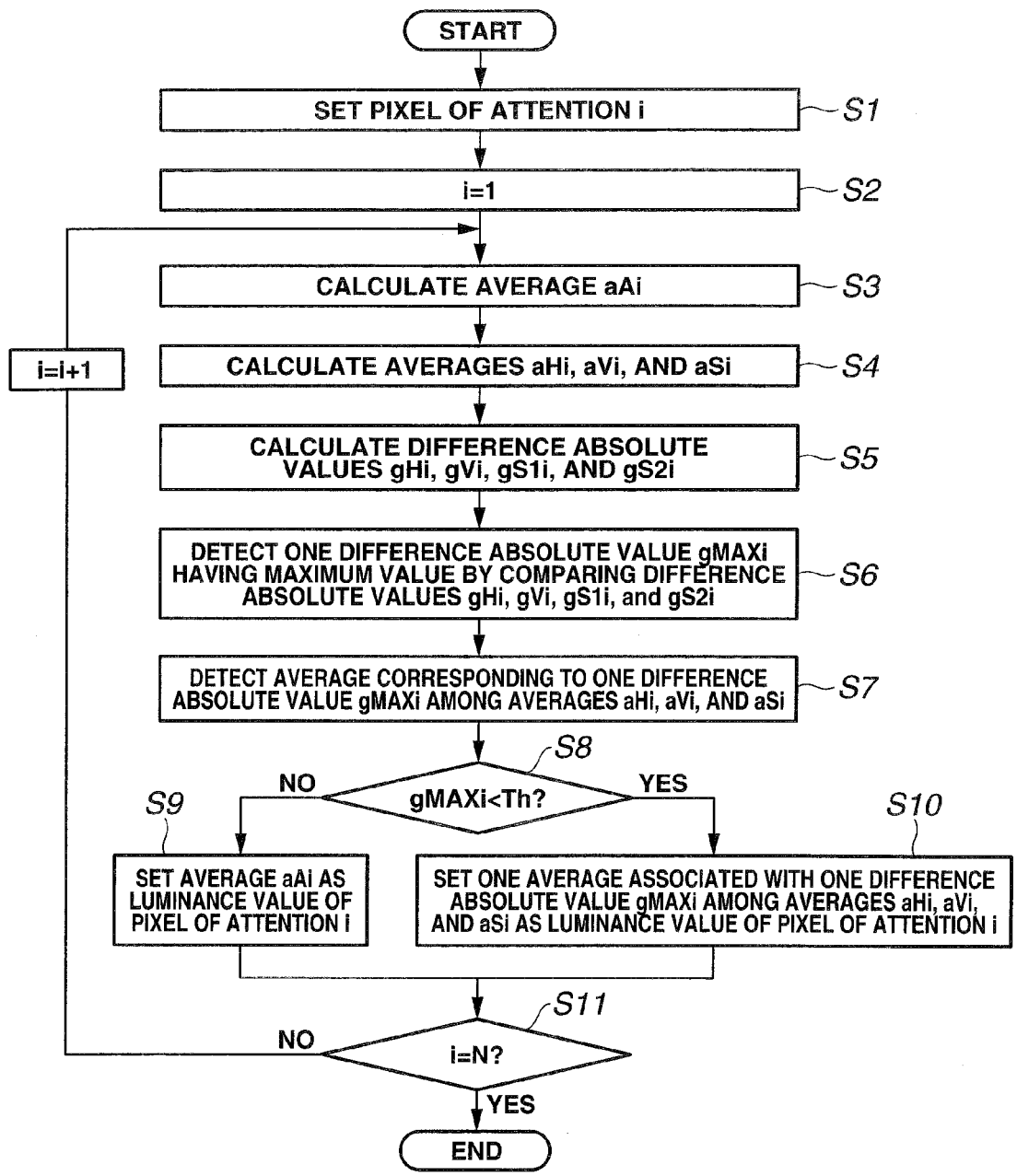

FIG.10
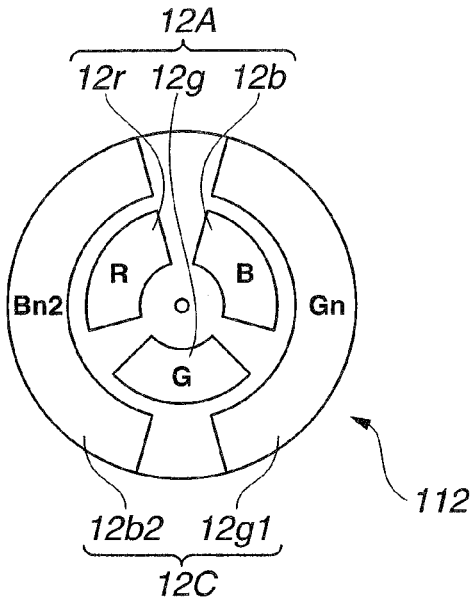
FIG.11
EXCITATION LIGHT CUT FILTER 22A
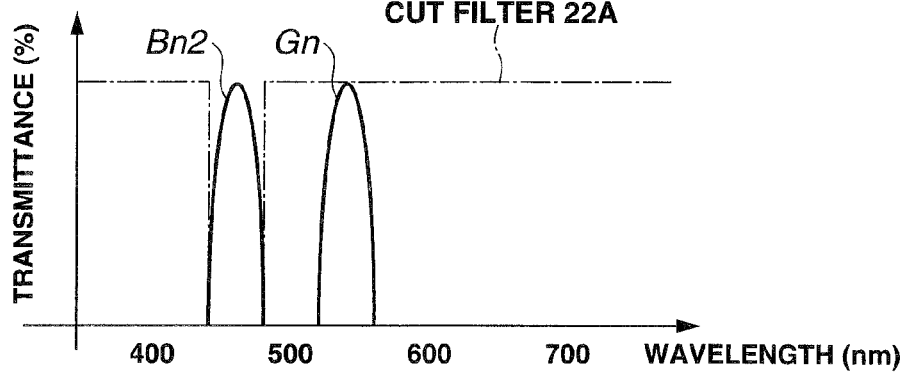
FIG.12
| 0 | 0 | 0 | 0 | 0 | 0 | 0 |
|---|---|---|---|---|---|---|
| 0 | 0 | 0 | 0 | 0 | 0 | 0 |
| 0 | 0 | 1 | 1 | 1 | 0 | 0 |
| 0 | 0 | 1 | 1 | 1 | 0 | 0 |
| 0 | 0 | 1 | 1 | 1 | 0 | 0 |
| 0 | 0 | 0 | 0 | 0 | 0 | 0 |
| 0 | 0 | 0 | 0 | 0 | 0 | 0 |

IMAGE GENERATING APPARATUS

CROSS REFERENCE TO RELATED APPLICATION

This application is a continuation application of PCT/JP2008/051908 filed on Feb. 6, 2008 and claims benefit of Japanese Application No. 2007-163074 filed in Japan on Jun. 20, 2007, the entire contents of which are incorporated herein by this reference.

BACKGROUND OF THE INVENTION

1. Field of the Invention

The present invention relates to an image generating apparatus, and, more particularly to an image generating apparatus that can acquire an image of autofluorescence emitted from a subject according to excitation light having a specific wavelength band and generate an image of the autofluorescence.

2. Description of the Related Art

An endoscope apparatus that can acquire an image of a subject in a specimen and generate an image of the subject is widely used in a medical field and the like in the past. In particular, an endoscope apparatus in the medical field is mainly used in an application in which a user performs treatment such as inspection and observation in a living organism.

As observation generally known as observation performed by using an endoscope apparatus in the medical field, for example, besides normal observation for irradiating white light on a subject in a living organism and acquiring an image of the subject substantially the same as that in visual observation, there is fluorescent observation for irradiating excitation light having a specific wavelength band on a subject in a living organism and acquiring an image of autofluorescence emitted from the subject according to the excitation light.

For example, an endoscope apparatus described in Japanese Patent Application Laid-Open Publication No. 2006-166940 has a configuration that can apply multilateral observation to a subject in a living organism while switching both observation modes of the normal observation and the fluorescent observation described above.

SUMMARY OF THE INVENTION

An image generating apparatus according to a first aspect of the present invention includes: a first light source unit that emits, as illumination light for illuminating a subject, light in a first wavelength band to the subject; a second light source unit that emits light in a second wavelength band, which is a part of the first wavelength band, to the subject; an image pickup unit that picks up an image of the subject and outputs the image as an image pickup signal; a light cut filter unit that is provided between the subject and the image pickup unit and cuts light in the second wavelength band reflected from the subject; and a complementary processing unit that applies, on the basis of the image pickup signal, complementary processing to a component equivalent to the second wavelength band cut by the light cut filter unit in the image of the subject picked up by the image pickup unit in a state in which the subject is illuminated by the light in the first wavelength band.

An image generating apparatus according to a second aspect of the present invention includes: a light source unit that emits light in a first wavelength band for illuminating a subject and light in a second wavelength band, which is a part of the first wavelength band; an image pickup unit that picks up an image of the subject and outputs the image as an image pickup signal; a light cut unit that is provided between the subject and the image pickup unit and cuts the light in the second wavelength band reflected from the subject; and a complementary processing unit that applies, on the basis of the image pickup signal, complementary processing to the image of the subject picked up by the image pickup unit with the second wavelength band cut by the light cut unit in the light emitted from the subject in a state in which the subject is illuminated by the light in the first wavelength band.

BRIEF DESCRIPTION OF THE DRAWINGS

FIG. 7 is a flowchart showing an example of processing performed by a noise reducing circuit shown in FIG. 1.

FIG. 8 is a diagram showing a positional relation between a pixel of attention and eight pixels adjacent to the pixel of attention.

FIG. 10 is a diagram showing an example of a specific configuration of a rotation filter shown in FIG. 9.

FIG. 11 is a diagram showing an example of transmission properties of filters included in a third filter group shown in FIG. 10 and a transmission property of an excitation light cut filter included in an endoscope shown in FIG. 9.

FIG. 12 is a diagram showing an example of a filter used by a contrast converting circuit shown in FIG. 9 in performing contrast conversion processing.

DETAILED DESCRIPTION OF THE PREFERRED EMBODIMENT(S)

Embodiments of the present invention are explained below with reference to the drawings.

First Embodiment

Figure 1:
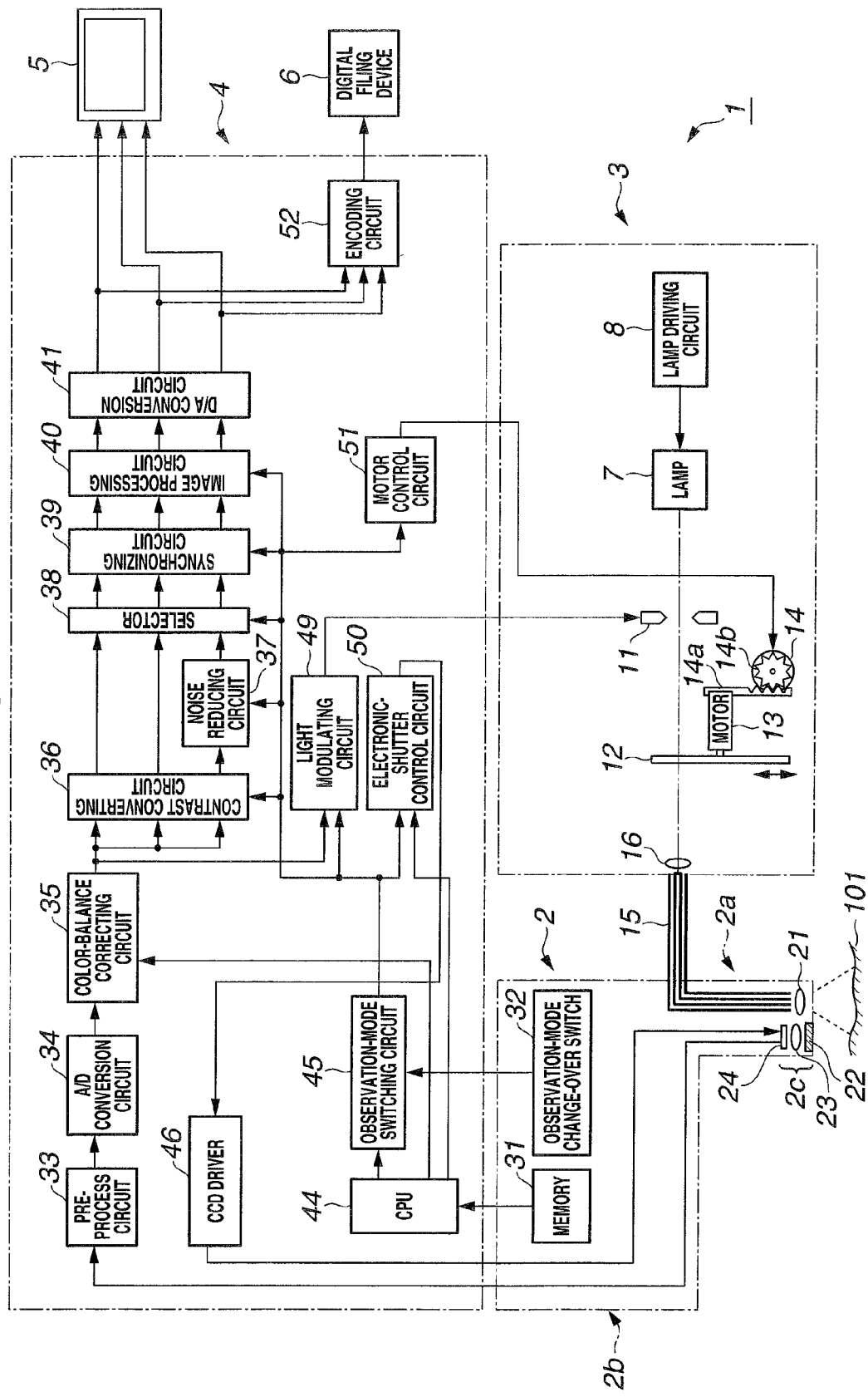
FIG. 1 is a diagram showing an example of a configuration of a main part of an endoscope apparatus according to a first embodiment of the present invention.
Figure 2:
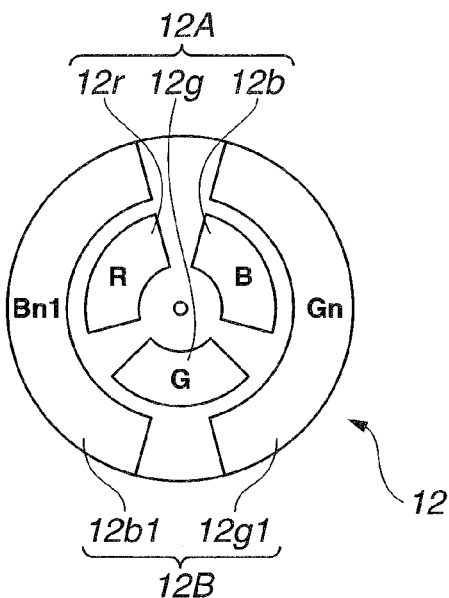
FIG. 2 is a diagram showing an example of a specific configuration of a rotation filter shown in FIG. 1.
Figure 3:
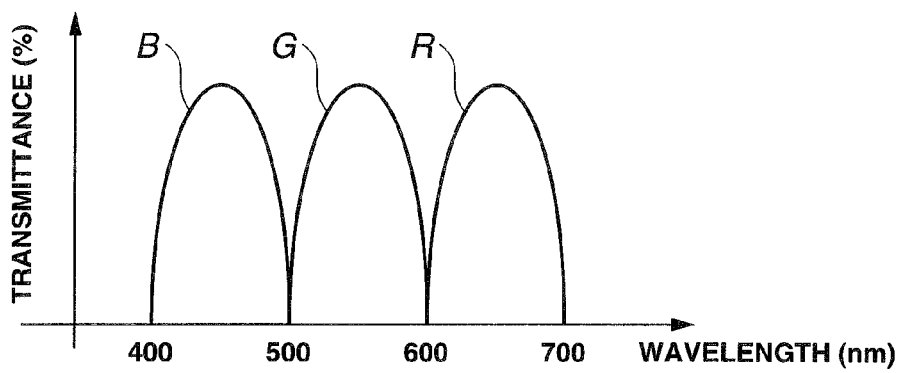
FIG. 3 is a diagram showing an example of transmission properties of filters included in a first filter group shown in FIG. 2.
Figure 4:
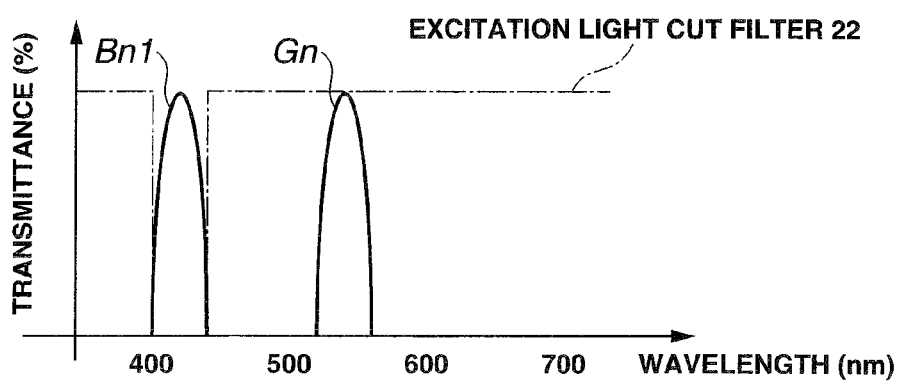
FIG. 4 is a diagram showing an example of transmission properties of filters included in a second filter group shown in FIG. 2 and a transmission property of an excitation light cut filter included in an endoscope shown in FIG. 1.
Figure 5:
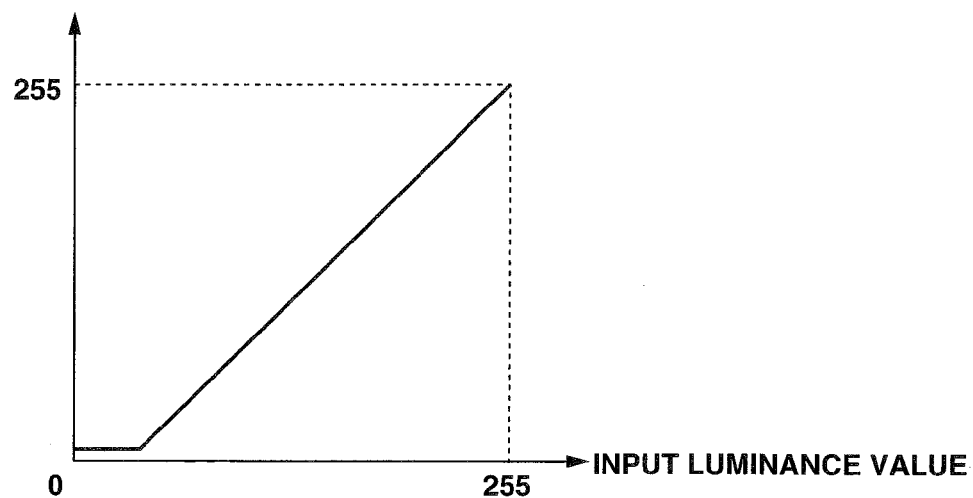
FIG. 5 is a diagram showing an example of a conversion table used by a contrast converting circuit shown in FIG. 1 in performing contrast conversion processing.
Figure 6:
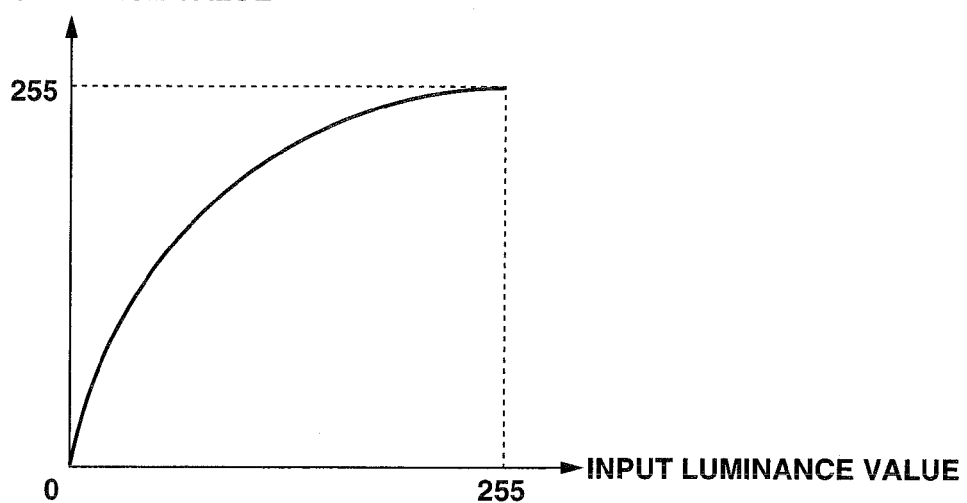
FIG. 6 is a diagram showing an example different from that shown in FIG. 5 of the conversion table used by the contrast converting circuit in performing the contrast conversion processing.

FIGS. 1 to 8 relate to a first embodiment of the present invention. FIG. 1 is a diagram showing an example of a configuration of a main part of an endoscope apparatus according to the first embodiment of the present invention. FIG. 2 is a diagram showing an example of a specific configuration of a rotation filter shown in FIG. 1. FIG. 3 is a diagram showing an example of transmission properties of filters included in a first filter group shown in FIG. 2. FIG. 4 is a diagram showing an example of transmission properties of filters included in a second filter group shown in FIG. 2 and a transmission property of an excitation light cut filter included in an endoscope shown in FIG. 1. FIG. 5 is a diagram showing an example of a conversion table used by a contrast converting circuit shown in FIG. 1 in performing contrast conversion processing. FIG. 6 is a diagram showing an example different from that shown in FIG. 5 of the conversion table used by the contrast converting circuit in performing the contrast conversion processing in FIG. 1. FIG. 7 is a flowchart showing an example of processing performed by a noise reducing circuit shown in FIG. 1. FIG. 8 is a diagram showing a positional relation between a pixel of attention and eight pixels adjacent to the pixel of attention.

In an endoscope apparatus 1 as an image generating apparatus according to the present embodiment, as shown in FIG. 1, a main part is configured to have an electronic endoscope 2 that is to be inserted into a living organism and picks up an image of a subject 101 in the living organism and outputs the image as an image pickup signal, a light source device 3 that emits illumination light for observation, a processor 4 that applies various kinds of signal processing to the image pickup signal outputted from the electronic endoscope 2, a monitor 5 that displays an image of the subject on the basis of a video signal outputted from the processor 4, and a digital filing device 6 that stores the image of the subject on the basis of image data outputted from the processor 4.

The electronic endoscope 2 has an elongated insertion section 2a to be inserted into a body cavity and an operation section 2b provided at a rear end of the insertion section 2a. A light guide 15 that transmits illumination light supplied from the light source device 3 to a distal end portion 2c of the insertion section 2a is inserted through an inside of the insertion section 2a. A not-shown light guide connector detachably connected to the light source device 3 is provided at a rear end of the light guide 15. With such a configuration, the illumination light supplied from the light source device 3 is transmitted by the light guide 15 and, after passing through an illumination optical system 21 provided at the distal end portion 2c of the insertion section 2a, emitted to the subject 101 in the living organism.

The light source device 3 as a light source unit has a lamp 7 such as a xenon lamp serving as a light source that emits white light, a lamp driving circuit 8 that drives the lamp 7 according to control by the processor 4, a stop 11 that is provided on an emission optical path of the lamp 7 and adjusts, according to the control by the processor 4, an emission amount of the white light emitted by the lamp 7, a rotation filter 12 that changes the white light, which has passed through the stop 11, to surface-sequential illumination light, a motor 13 that rotates the rotation filter 12 according to the control by the processor 4, a motor 14 that moves the rotation filter 12 and the rotation motor 13 in a direction perpendicular to the emission optical path of the lamp 7 according to the control by the processor 4, and a condensing optical system 16 that condenses the illumination light, which has passed through the rotation filter 12, and supplies the illumination light to an incident side end face of the light guide 15 connected to the light source device 3.

As shown in FIG. 2, the rotation filter 12 is configured in a disc shape with a rotation axis set as a center and has a first filter group 12A including plural filters provided along a circumferential direction on an inner circumferential side and a second filter group 12B including plural filters provided along a circumferential direction on an outer circumferential side. In the rotation filter 12, portions other than portions where the filters of the first filter group 12A and the second filter group 12B are arranged are configured by a member that blocks light.

The first filter group 12A is configured to have an R filter 12r that transmits light in a wavelength band for red, a G filter 12g that transmits light in a wavelength band for green, and a B filter 12b that transmits light in a wavelength band for blue, each of which is provided along the circumferential direction on the inner circumferential side of the rotation filter 12.

The R filter 12r has a configuration for mainly transmitting, for example, as shown in FIG. 3, light (R light) from 600 nm to 700 nm as light in a wavelength band of a red region. The G filter 12g has a configuration for mainly transmitting, for example, as shown in FIG. 3, light (G light) from 500 nm to 600 nm as light in a wavelength band of a green region. Further, the B filter 12b has a configuration for mainly transmitting, for example, as shown in FIG. 3, light (B light) from 400 nm to 500 nm as light in a wavelength band of a blue region.

The second filter group 12B is configured to have a Bn1 filter 12b1 that transmits light in a blue and narrow band and a Gn filter 12g1 that transmits light in a green and narrow band, each of which is provided along the circumferential direction on the outer circumferential side of the rotation filter 12.

The Bn1 filter 12b1 has a configuration for transmitting, for example, as shown in FIG. 4, light (Bn1 light) on a short wavelength side of the B light as the light in the blue and narrow band and light that can cause the subject 101 to generate autofluorescence.

The Gn filter 12g1 has a configuration for transmitting, for example, as shown in FIG. 4, light (Gn light) having a wavelength near 540 nm as the light in the green and narrow band.

In the light source device 3 shown in FIG. 1, a rack 14a is attached to the motor 13 and a pinion 14b is attached to the motor 14. The rack 14a is attached to screw in the pinion 14b. With such a configuration, the rack 14a moves in association with the rotation of the motor 14 and the pinion 14b. The rotation filter 12 and the rotation motor 13 move in an arrow direction (a direction perpendicular to the emission optical path of the lamp 7) in FIG. 1 in association with the movement of the rack 14a.

On the other hand, at the distal end portion 2c of the insertion section 2a, the illumination optical system 21 that emits illumination light, which is transmitted by the light guide 15, to the subject 101, an excitation light cut filter 22, an object optical system 23 that forms an image of the subject 101 that passes through the excitation light cut filter 22, and a CCD (charge coupled device) 24 arranged in an image-forming position of the object optical system 23 are provided.

The excitation light cut filter 22 as a light cut filter unit is an optical element that is arranged on a light incident side of the object optical system 23 (at a pre-stage of the CCD 24) and set such that transmittance of a wavelength band of the Bn1 light described above is substantially 0. In other words, the excitation light cut filter 22 has a configuration for cutting the Bn1 light reflected from the subject 101. An example of a transmission property of the excitation light cut filter 22 in the present embodiment is shown in FIG. 4.

The CCD 24 as an image pickup unit is driven according to a driving signal outputted from the processor 4, picks up an image of the subject 101 that has passed through the excitation light cut filter 22 (and the object optical system 23), and outputs the picked up image of the subject 101 to the processor 4 as an image pickup signal.

In the operation section 2b of the electronic endoscope 2, a memory 31 in which information of such as an apparatus model, an ID, a parameter for color balance correction, and electronic shutter speed is stored as endoscope information of the electronic endoscope 2 and an observation-mode change-over switch 32 that can output, according to operation by a user, an instruction signal for switching an observation mode of the endoscope apparatus 1 to a normal observation mode and a fluorescent observation mode are provided.

The processor 4 has a pre-process circuit 33, an A/D conversion circuit 34, a color-balance correcting circuit 35, a contrast converting circuit 36, a noise reducing circuit 37, a selector 38, a synchronizing circuit 39, an image processing circuit 40, a D/A conversion circuit 41, and an encoding circuit 52.

The pre-process circuit 33 applies pre-processing such as amplification processing to the image pickup signal from the CCD 24 and outputs the image pickup signal.

The A/D conversion circuit 34 applies A/D conversion to the image pickup signal from the pre-process circuit 33 and outputs the image pickup signal.

The color-balance correcting circuit 35 has a not-shown matrix circuit and a not-shown AGC circuit. The color-balance correcting circuit 35 applies, on the basis of control by a CPU 44 described later, color balance processing such as white balance and gain adjustment to the image pickup signal from the A/D conversion circuit 34 while applying the parameter for color balance correction included in the endoscope information described above to the matrix circuit and the AGC circuit and outputs the image pickup signal.

The contrast converting circuit 36 as a complementary processing unit applies, on the basis of control by an observation-mode switching circuit 45 described later, as complementary processing, contrast conversion processing described later to a component of an image of the B light (hereinafter abbreviated as B component) in the image of the subject 101 corresponding to the image pickup signal from the color-balance correcting circuit 35 and outputs the B component.

The noise reducing circuit 37 as a noise-reduction processing unit applies, on the basis of the control by the observation-mode switching circuit 45 described later, noise reduction processing described later to the B component outputted via the contrast converting circuit 36 in the image of the subject 101 corresponding to the image pickup signal from the color-balance correcting circuit 35 and outputs the B component.

The selector 38 selectively outputs the image pickup signal corresponding to each of the observation modes on the basis of the control by the observation-mode switching circuit 45 described later.

The synchronizing circuit 39 is configured to have a frame memory and the like and outputs, on the basis of the control by the observation-mode switching circuit 45 described later and a not-shown timing generator provided in the observation-mode switching circuit 45, the image pickup signal from the selector 38 frame by frame while synchronizing the image pickup signal.

The image processing circuit 40 applies, on the basis of the control by the observation-mode switching circuit 45 described later, image processing such as enhancement processing to the image pickup signal from the synchronizing circuit 39 and outputs the image pickup signal.

The D/A conversion circuit 41 applies D/A conversion to the image pickup signal from the image processing circuit 40 and outputs the image pickup signal after the D/A conversion as a video signal. Consequently, an image of the subject 101 corresponding to the video signal is displayed on the monitor 5 as an image.

The encoding circuit 52 applies encoding processing (such as compression processing) to the image pickup signal from the D/A conversion circuit 41 and outputs the image pickup signal after the encoding processing as image data. Consequently, an image of the subject 101 corresponding to the image data is stored in the digital filing device 6.

The processor 4 has a CPU 44, an observation-mode switching circuit 45, a CCD driver 46, a light modulating circuit 49, an electronic-shutter control circuit 50, and a motor control circuit 51.

The CPU 44 reads endoscope information stored in the memory 31 of the electronic endoscope 2 and applies control based on the read endoscope information to the units of the processor 4.

The observation-mode switching circuit 45 performs, on the basis of an instruction signal from the observation-mode change-over switch 32 and the control by the CPU 44, control for switching an observation mode of the processor 4 to the normal observation mode or the fluorescent observation mode. The observation-mode switching circuit 45 has a not-shown timing generator that can generate a timing signal for instructing timing when the units of the processor 4 perform processing or operation.

The CCD driver 46 outputs a driving signal on the basis of control by the electronic-shutter control circuit 50 to thereby control a driving state of the CCD 24 such that timing when an image of the subject 101 is picked up is predetermined timing described later.

The light modulating circuit 49 controls, on the basis of the image pickup signal from the color-balance correcting circuit 35 and the control by the observation-mode switching circuit 45, a stop amount of the stop 11 such that illumination light emitted from the light source device 3 has an appropriate light amount.

The electronic-shutter control circuit 50 applies, on the basis of the control by the CPU 44 and the observation-mode switching circuit 45, control for causing the CCD driver 46 to output a driving signal at every predetermined timing corresponding to electronic shutter speed included in the endoscope information described above to the CCD driver 46 such that the electronic shutter speed and charge accumulation time in the CCD 24 substantially coincide with each other.

The motor control circuit 51 controls the motor 14 on the basis of the control by the observation-mode switching circuit 45 to thereby change a filter group arranged on the emission optical path of the lamp 7 to the first filter group 12A or the second filter group 12B. Illumination light corresponding to the observation mode of the processor 4 is emitted from the light source device 3 according to the control performed by the motor control circuit 51.

Next, actions of the endoscope apparatus 1 according to the present embodiment are explained.

First, the user turns on a power supply for the units of the endoscope apparatus 1, i.e., the endoscope 2, the light source device 3, the processor 4, the monitor 5, and the digital filing device 6 and sets the units in an activated state. It is assumed that, in the activated state, i.e., a state immediately after the power supply is turned on, the endoscope 2, the light source device 3, and the video processor 4 are set in the normal observation mode.

When the processor 4 is set in the normal observation mode, the observation-mode switching circuit 45 applies, on the basis of an instruction signal outputted from the observation-mode change-over switch 32, control for causing the units of the processor 4 to perform operation corresponding to the normal observation mode.

The motor control circuit 51 controls the motor 14 on the basis of the control by the observation-mode switching circuit 45 to thereby arrange the first filter group 12A on the emission optical path of the lamp 7. Consequently, surface-sequential illumination light of R light, G light, and B light is repeatedly emitted from the light source device 3 as illumination light corresponding to the observation mode of the processor 4. The surface-sequential illumination light of the R light, the G light, and the B light is emitted to the subject 101 through the illumination optical system 21 after being transmitted by the light guide 15.

On the other hand, the CCD 24 operates according to a driving signal outputted from the CCD driver 46, picks up, at every predetermined timing, an image of the subject 101 sequentially illuminated by the R light, the G light, and the B light, and outputs the picked-up image of the subject 101 to the pre-process circuit 33 as an image pickup signal.

The image pickup signal outputted from the CCD 24 is inputted to the contrast converting circuit 36 and the light modulating circuit 49 after being subjected to pre-processing by the pre-process circuit 33, subjected to A/D conversion by the A/D conversion circuit 34, and subjected to color balance processing by the color-balance correcting circuit 35.

The light modulating circuit 49 controls a stop amount of the stop 11 on the basis of the image pickup signal from the color-balance correcting circuit 35 and the control by the observation-mode switching circuit 45 such that illumination light emitted from the light source device 3 has a light amount suitable for normal observation.

On the other hand, the contrast converting circuit 36 applies contrast conversion processing to a B component on the basis of the control by the observation-mode switching circuit 45 while putting through a component of an image of the R light (hereinafter abbreviated as R component) and a component of an image of the G light (hereinafter abbreviated as G component) in the image of the subject 101 corresponding to the image pickup signal from the color-balance correcting circuit 35.

The B component inputted to the contrast converting circuit 36 is a component, a band on a short wavelength side of which is cut by the excitation light cut filter 22. Therefore, for example, when capillaries of a surface layer of a living tissue are included in the subject 101, contrast between a portion with a large hemoglobin amount (a portion of the capillaries) and a portion with a small hemoglobin amount (a portion other than the capillaries) is reduced. As a result, an image of the subject 101 that makes observation difficult is outputted.

In view of the point described above, the contrast converting circuit 36 according to the present embodiment performs, as contrast conversion processing, processing for converting the luminance of the inputted B component and outputting the B component using, for example, a conversion table shown in FIG. 5. Specifically, the contrast converting circuit 36 performs, as contrast conversion processing, processing for outputting the inputted B component while reducing a black level in the luminance of the B component using the conversion table shown in FIG. 5.

When the contrast converting circuit 36 performs the contrast conversion processing, the contrast between the portion with a large hemoglobin amount and the portion with a small hemoglobin amount is improved in the image of the subject 101 acquired in the normal observation mode.

The contrast converting circuit 36 is not limited to a circuit that performs, as the contrast conversion processing, the processing employing the conversion table shown in FIG. 5 and may be a circuit that performs, for example, processing employing a conversion table complying with gamma conversion shown in FIG. 6.

The noise reducing circuit 37 applies, on the basis of the control by the observation-mode switching circuit 45, noise reduction processing to the B component subjected to the contrast conversion processing described above.

A specific example of the noise reduction processing by the noise reducing circuit 37 is explained.

First, the noise reducing circuit 37 sets a pixel of attention i in the B component from the contrast converting circuit 36 and sets a value of i to 1 (step S1 and step S2 in FIG. 7).

In the present embodiment, it is assumed that the B component from the contrast converting circuit 36 has N pixels. Therefore, it is assumed that the variable i is an integer that satisfies $1 \leq i \leq N$.

Thereafter, the noise reducing circuit 37 detects the pixel of attention i and eight pixels (a pixel i1 to a pixel i8) adjacent to the pixel of attention, which have a positional relation shown in FIG. 8 with each other, and calculates an average of luminances of these nine pixels as an average aAi (step S3 in FIG. 7).

The noise reducing circuit 37 calculates an average of luminances of six pixels i1, i3, i4, i5, i6, and i8 as an average aHi, calculates an average of luminances of six pixels i1, i2, i3, i6, i7, and i8 as an average aVi, and calculates an average of luminances of four pixels i2, i4, i5, and i7 as an average aSi (step S4 in FIG. 7).

Further, the noise reducing circuit 37 calculates an absolute value |AbsH| of a value AbsH, which is obtained by subtracting an average of luminances of three pixels i3, i5, and i8 from an average of luminances of three pixels i1, i4, and i6, as a difference absolute value gHi and calculates an absolute value |AbsV| of a value AbsV, which is obtained by subtracting an average of luminances of three pixels i6, i7, and i8 from an average of luminances of three pixels i1, i2, and i3, as a difference absolute value gVi (step S5 in FIG. 7). The noise reducing circuit 37 calculates an absolute value |AbsS1| of a value AbsS1, which is obtained by subtracting an average of luminances of two pixels i5 and i7 from an average of luminances of two pixels i2 and i4, as a difference absolute value gS1 and calculates an absolute value |AbsS2| of a value AbsS2, which is obtained by subtracting an average of luminances of two pixels i4 an i7 from an average of luminances of two pixels i2 and i5, as a difference absolute value gS2i (step S5 in FIG. 7).

The noise reducing circuit 37 compares the difference absolute values gHi, gVi, gS1i, and gS2i calculated in step S5 in FIG. 7 to thereby detect one difference absolute value gMAXi having a maximum value among the difference absolute values (step S6 in FIG. 7).

Thereafter, the noise reducing circuit 37 detects an average corresponding to the one difference absolute value gMAXi among the averages aHi, aVi, and aSi (step S7 in FIG. 7).

Specifically, when the one difference absolute value gMAXi is the difference absolute value gHi, the noise reducing circuit 37 detects the average aHi as a processing result in step S7 in FIG. 7. When the one difference absolute value gMAXi is the difference absolute value gVi, the noise reducing circuit 37 detects the average aVi as a processing result in step S7 in FIG. 7. Further, when the one difference absolute value gMAXi is the difference absolute value gS1i or gS2i, the noise reducing circuit 37 detects the average aSi as a processing result in step S7 in FIG. 7.

The noise reducing circuit 37 detects whether the one difference absolute value gMAXi is smaller than a threshold Th (step S8 in FIG. 7). When the noise reducing circuit 37 detects that the one difference absolute value gMAXi is smaller than the threshold Th, the noise reducing circuit 37 determines that the pixel of attention i is not a pixel forming an edge and sets the average aAi as a luminance value of the pixel of attention i (step S9 in FIG. 7). When the noise reducing circuit 37 detects that the one difference absolute value gMAXi is equal to or larger than the threshold Th, the noise reducing circuit 37 determines that the pixel of attention i is a pixel forming an edge and sets one average associated with the one difference absolute value gMAXi among the averages aHi, aVi, and aSi as a luminance value of the pixel of attention i (step S10 in FIG. 7).

Specifically, when the one difference absolute value gMAXi is the difference absolute value gHi and the noise reducing circuit 37 detects that the difference absolute value gHi is equal to or larger than the threshold Th, the noise reducing circuit 37 determines that the pixel of attention i is a pixel forming an edge in the vertical direction and sets the average aHi as a luminance value of the pixel of attention i.

When the one difference absolute value gMAXi is the difference absolute value gVi and the noise reducing circuit 37 detects that the difference absolute value gVi is equal to or larger than the threshold Th, the noise reducing circuit 37 determines that the pixel of attention i is a pixel forming an edge in the horizontal direction and sets the average aVi as a luminance value of the pixel of attention i.

When the one difference absolute value gMAXi is the difference absolute value gS1i and the noise reducing circuit 37 detects that the difference absolute value gS1i is equal to or larger than the threshold Th, the noise reducing circuit 37 determines that the pixel of attention i is a pixel forming an edge in an oblique direction and sets the average aSi as a luminance value of the pixel of attention i.

Further, when the one difference absolute value gMAXi is the difference absolute value gS2i and the noise reducing circuit 37 detects that the difference absolute value gS2i is equal to or larger than the threshold Th, the noise reducing circuit 37 determines that the pixel of attention i is a pixel forming an edge in an oblique direction and sets the average aSi as a luminance value of the pixel of attention i.

When the noise reducing circuit 37 detects that the variable i is not N (step S11 in FIG. 7), the noise reducing circuit 37 repeatedly performs the processing from step S3 to step S11 in FIG. 7 while adding 1 to a value of the variable i (step S12 in FIG. 7). When the noise reducing circuit 37 detects that the variable i is N (step S11 in FIG. 7), the noise reducing circuit 37 ends the series of noise reduction processing.

When the noise reducing circuit 37 performs the noise reduction processing described above, in particular, noise that occurs in an edge portion in the image of the subject 101 acquired in the normal observation mode can be reduced.

The R component and the G component outputted from the contrast converting circuit 36 and the B component outputted from the noise reducing circuit 37 are outputted to the monitor 5 after being transmitted through the selector 38, synchronized by the synchronizing circuit 39, subjected to image processing by the image processing circuit 40, and subjected to D/A conversion by the D/A conversion circuit 41.

When the processing and the like described above are performed in the processor 4, an image of the subject 101 in which hues obtained when the endoscope 2 does not have the excitation light cut filter 22 are reproduced is displayed on the monitor 5 as an image.

The user operates the observation-mode change-over switch 32 to thereby switch the observation mode of the endoscope apparatus 1 from the normal observation mode to the fluorescent observation mode.

When the processor 4 is set in the fluorescent observation mode, the observation-mode switching circuit 45 applies, on the basis of an instruction signal outputted from the observation-mode change-over switch 32, control for causing the units of the processor 4 to perform operation corresponding to the fluorescent observation mode.

The motor control circuit 51 controls the motor 14 on the basis of the control by the observation-mode switching circuit 45 to thereby arrange the second filter group 12B on the emission optical path of the lamp 7. Consequently, surface-sequential illumination light of Bn1 light and Gn light is repeatedly emitted from the light source device 3 as illumination light corresponding to the observation mode of the processor 4. The surface-sequential illumination light of the Bn1 light and the Gn light is emitted to the subject 101 through the illumination light optical system 21 after being transmitted by the light guide 15.

On the other hand, the CCD 24 operates according to a driving signal outputted from the CCD driver 46, picks up, at every predetermined timing, an image of the subject 101 sequentially illuminated by the Bn1 light and the Gn light, and outputs the picked-up image of the subject 101 to the pre-process circuit 33 as an image pickup signal.

The image pickup signal outputted from the CCD 24 is inputted to the contrast converting circuit 36 and the light modulating circuit 49 after being subjected to pre-processing by the pre-process circuit 33, subjected to A/D conversion by the A/D conversion circuit 34, and subjected to color balance processing by the color-balance correcting circuit 35.

A component of an image of the Bn1 light and a component of an image of the Gn light of an image pickup signal in fluorescent observation are outputted in a state in which the components are converted into components of red, green, and blue by the color balance processing of the color-balance correcting circuit 35.

The light modulating circuit 49 controls a stop amount of the stop 11 on the basis of the image pickup signal from the color-balance correcting circuit 35 and the control by the observation-mode switching circuit 45 such that illumination light emitted from the light source device 3 has a light amount suitable for fluorescent observation.

In the fluorescent observation mode, the contrast converting circuit 36 and the noise reducing circuit 37 output the inputted image pickup signal to the selector 38 while putting through the image pickup signal.

Thereafter, the image pickup signal transmitted through the selector 38 is outputted to the monitor 5 while being synchronized by the synchronizing circuit 39, subjected to image processing by the image processing circuit 40, and subjected to D/A conversion by the D/A conversion circuit 41. Consequently, an image of fluorescent light emitted by the subject 101 is displayed on the monitor 5.

As explained above, in the endoscope apparatus 1 according to the present embodiment, in the normal observation mode, processing for complementing a hue of a band cut by the excitation light cut filter 22 is performed. Therefore, in the normal observation mode, the endoscope apparatus 1 according to the present embodiment can acquire an image of the subject 101 in which hues obtained when the excitation light cut filter 22 is not provided between the subject 101 and the CCD 24 are reproduced.

Second Embodiment

Figure 9:
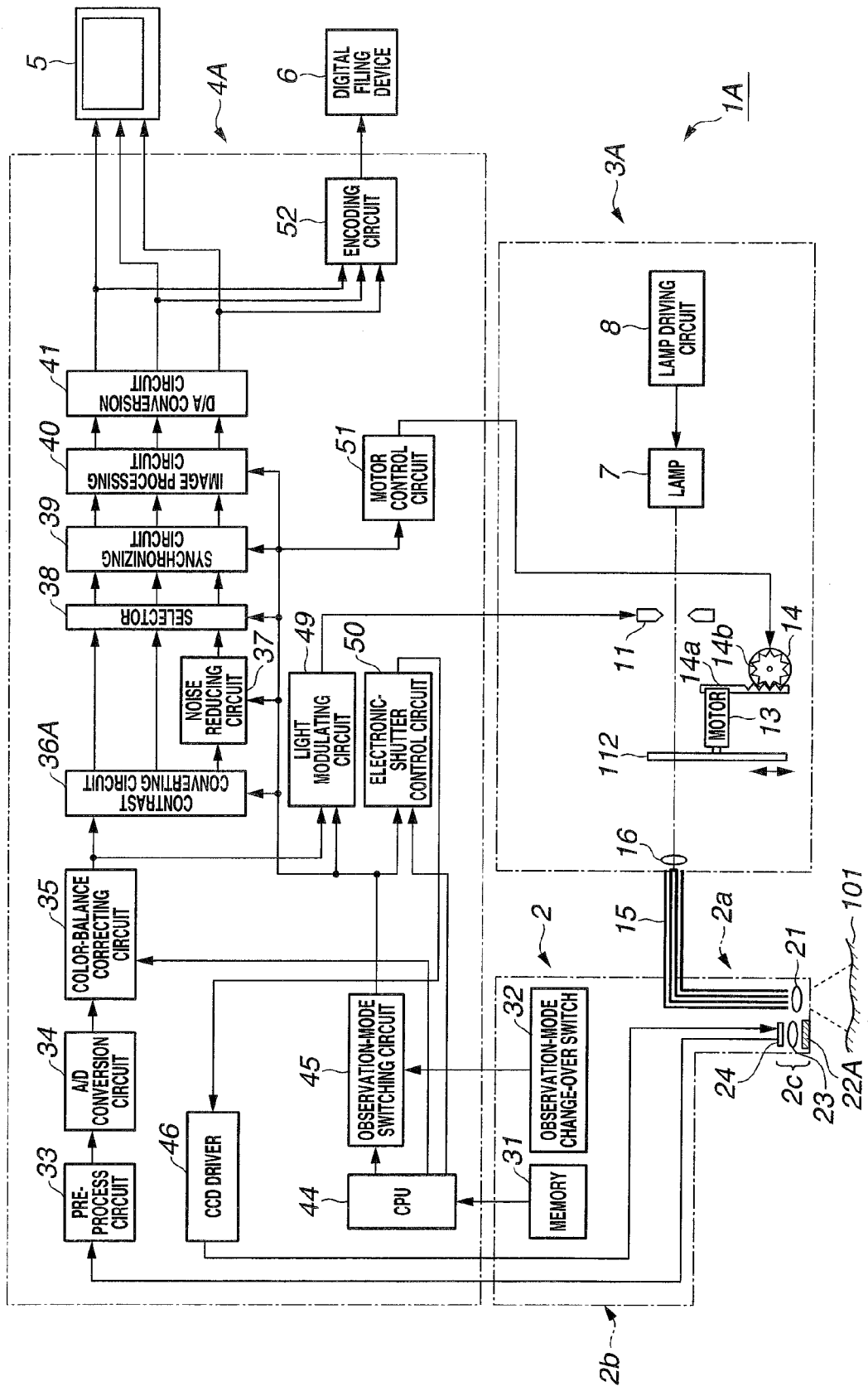
FIG. 9 is a diagram showing an example of a configuration of a main part of an endoscope apparatus according to a second embodiment of the present invention.

FIGS. 9 to 12 relate to the second embodiment of the present invention. FIG. 9 is a diagram showing an example of a configuration of a main part of an endoscope apparatus according to a second embodiment of the present invention. FIG. 10 is a diagram showing an example of a specific configuration of a rotation filter shown in FIG. 9. FIG. 11 is a diagram showing an example of transmission properties of filters included in a third filter group shown in FIG. 10 and a transmission property of an excitation light cut filter included in an endoscope shown in FIG. 9. FIG. 12 is a diagram showing an example of a filter used by a contrast converting circuit shown in FIG. 9 in performing contrast conversion processing.

Concerning components having the same configurations as those in the first embodiment, detailed explanation is omitted. A configuration of the endoscope apparatus according to the present embodiment is substantially the same as the configuration of the endoscope apparatus according to the first embodiment. Therefore, components having configurations or actions different from those in the endoscope apparatus according to the first embodiment are mainly explained below.

In an endoscope apparatus 1A as an image generating apparatus according to the present embodiment, as shown in FIG. 9, a main part is configured to have an electronic endoscope 2A in which an excitation light cut filter 22A is provided instead of the excitation light cut filter 22 in the electronic endoscope 2, a light source device 3A in which a rotation filter 112 is provided instead of the rotation filter 12 in the light source device 3, a processor 4A in which a contrast converting circuit 36A is provided instead of the contrast converting circuit 36 in the processor 4, the monitor 5, and the digital filing device 6.

The rotation filter 112 of the light source device 3A as a light source unit has, as shown in FIG. 10, the first filter group 12A and a third filter group 12C including plural filters provided along a circumferential direction on an outer circumference side. In the rotation filter 112, portions other than portions where the filters of the first filter group 12A and the third filter group 12C are arranged are configured by a member that blocks light.

The third filter group 12C is configured to have a Bn2 filter 12b2 that transmits light in a blue and narrow band and the Gn filter 12g1, each of which is provided along the circumferential direction on the outer circumference side of the rotation filter 112.

The Bn filter 12b2 has a configuration for transmitting, for example, as shown in FIG. 11, light (Bn2 light) on a long wavelength side of the B light as blue, narrowband light that can generate autofluorescence in the subject 101.

The excitation light cut filter 22A as a light cut filter unit is an optical element arranged on the light incident side of the object optical system 23 (at the pre-stage of the CCD 24) and set such that the transmittance of a wavelength band of the Bn2 light is substantially 0. In other words, the excitation light cut filter 22A has a configuration for cutting the Bn2 light reflected from the subject 101. An example of the transmittance of the excitation light cut filter 22A in the present embodiment is shown in FIG. 11.

The contrast converting circuit 36A as a complementary processing unit applies, on the basis of the control by the observation-mode switching circuit 45, contrast conversion processing described later to the B component in the image of the subject 101 corresponding to the image pickup signal from the color-balance correcting circuit 35 as complementary processing and outputs the B component.

Next, actions of the endoscope apparatus 1A according to the present embodiment are explained.

First, a user turns on a power supply for the units of the endoscope apparatus 1A, i.e., the endoscope 2A, the light source device 3A, the processor 4A, the monitor 5, and the digital filing device 6 and sets the units in an activated state. It is assumed that, in the activated state, i.e., a state immediately after the power supply is turned on, the endoscope 2A, the light source device 3A, and the video processor 4A are set in the normal observation mode.

When the processor 4A is set in the normal observation mode, the observation-mode switching circuit 45 applies, on the basis of an instruction signal outputted from the observation-mode change-over switch 32, control for causing the units of the processor 4A to perform operation corresponding to the normal observation mode.

The motor control circuit 51 controls the motor 14 on the basis of the control by the observation-mode switching circuit 45 to thereby arrange the first filter group 12A on the emission optical path of the lamp 7. Consequently, surface-sequential illumination light of R light, G light, and B light is repeatedly emitted from the light source device 3A as illumination light corresponding to the observation mode of the processor 4A. The surface-sequential illumination light of the R light, the G light, and the B light is emitted to the subject 101 through the illumination optical system 21 after being transmitted by the light guide 15.

On the other hand, the CCD 24 operates according to a driving signal outputted from the CCD driver 46, picks up, at every predetermined timing, an image of the subject 101 sequentially illuminated by the R light, the G light, and the B light, and outputs the picked-up image of the subject 101 to the pre-process circuit 33 as an image pickup signal.

The image pickup signal outputted from the CCD 24 is inputted to the contrast converting circuit 36A and the light modulating circuit 49 after being subjected to pre-processing by the pre-process circuit 33, subjected to A/D conversion by the A/D conversion circuit 34, and subjected to color balance processing by the color-balance correcting circuit 35.

The light modulating circuit 49 controls a stop amount of the stop 11 on the basis of the image pickup signal from the color-balance correcting circuit 35 and the control by the observation-mode switching circuit 45 such that illumination light emitted from the light source device 3 has a light amount suitable for normal observation.

On the other hand, the contrast converting circuit 36A applies contrast conversion processing to a B component on the basis of the control by the observation-mode switching circuit 45 while putting through an R component and a G component in the image of the subject 101 corresponding to the image pickup signal from the color-balance correcting circuit 35.

The B component inputted to the contrast converting circuit 36 is a component, a band on a long wavelength side of which is cut by the excitation light cut filter 22A. Therefore, for example, when capillaries of a surface layer of a living tissue are included in the subject 101, contrast between a portion with a large hemoglobin amount (a portion of the capillaries) and a portion with a small hemoglobin amount (a portion other than the capillaries) excessively increases. As a result, an image of the subject 101 that makes observation difficult is outputted.

In view of the point described above, the contrast converting circuit 36 according to the present embodiment performs, as contrast conversion processing, processing for converting the luminance of the inputted B component and outputting the B component using, for example, a conversion table shown in FIG. 5. Specifically, the contrast converting circuit 36A performs, as contrast conversion processing, processing for outputting the inputted B component while reducing contrast of a portion of capillaries in the B component using the low-pass filter shown in FIG. 5.

When the contrast converting circuit 36A performs the contrast conversion processing described above, the contrast between the portion with a large hemoglobin amount and the portion with a small hemoglobin amount is improved in the image of the subject 101 acquired in the normal observation mode.

Thereafter, the B component outputted from the contrast converting circuit 36A is inputted to the selector 38 after being subjected to the noise reduction processing described in the explanation of the first embodiment by the noise reducing circuit 37.

The R component and the G component outputted from the contrast converting circuit 36A and the B component outputted from the noise reducing circuit 37 are outputted to the monitor 5 after being transmitted through the selector 38, synchronized by the synchronizing circuit 39, subjected to image processing by the image processing circuit 40, and subjected to D/A conversion by the D/A conversion circuit 41.

When the processing and the like described above are performed in the processor 4A, an image of the subject 101 in which hues obtained when the endoscope 2A does not have the excitation light cut filter 22A are reproduced is displayed on the monitor 5 as an image.

The user operates the observation-mode change-over switch 32 to thereby switch the observation mode of the endoscope apparatus 1A from the normal observation mode to the fluorescent observation mode.

When the processor 4A is set in the fluorescent observation mode, the observation-mode switching circuit 45 applies, on the basis of an instruction signal outputted from the observation-mode change-over switch 32, control for causing the units of the processor 4A to perform operation corresponding to the fluorescent observation mode.

The motor control circuit 51 controls the motor 14 on the basis of the control by the observation-mode switching circuit 45 to thereby arrange the third filter group 12C on the emission optical path of the lamp 7. Consequently, surface-sequential illumination light of Bn2 light and Gn light is repeatedly emitted from the light source device 3A as illumination light corresponding to the observation mode of the processor 4A. The surface-sequential illumination light of the Bn2 light and the Gn light is emitted to the subject 101 through the illumination light optical system 21 after being transmitted by the light guide 15.

On the other hand, the CCD 24 operates according to a driving signal outputted from the CCD driver 46, picks up, at every predetermined timing, an image of the subject 101 sequentially illuminated by the Bn2 light and the Gn light, and outputs the picked-up image of the subject 101 to the pre-process circuit 33 as an image pickup signal.

The image pickup signal outputted from the CCD 24 is inputted to the contrast converting circuit 36A and the light modulating circuit 49 after being subjected to pre-processing by the pre-process circuit 33, subjected to A/D conversion by the A/D conversion circuit 34, and subjected to color balance processing by the color-balance correcting circuit 35.

A component of an image of the Bn2 light and a component of an image of the Gn light of an image pickup signal in fluorescent observation are outputted in a state in which the components are converted into components of red, green, and blue by the color balance processing of the color-balance correcting circuit 35.

The light modulating circuit 49 controls a stop amount of the stop 11 on the basis of the image pickup signal from the color-balance correcting circuit 35 and the control by the observation-mode switching circuit 45 such that illumination light emitted from the light source device 3A has a light amount suitable for fluorescent observation.

In the fluorescent observation mode, the contrast converting circuit 36A and the noise reducing circuit 37 output the inputted image pickup signal to the selector 38 while putting through the image pickup signal.

Thereafter, the image pickup signal transmitted through the selector 38 is outputted to the monitor 5 while being synchronized by the synchronizing circuit 39, subjected to image processing by the image processing circuit 40, and subjected to D/A conversion by the D/A conversion circuit 41. Consequently, an image of fluorescent light emitted by the subject 101 is displayed on the monitor 5.

As explained above, in the endoscope apparatus 1A according to the present embodiment, in the normal observation mode, processing for complementing a hue of a band cut by the excitation light cut filter 22A is performed. Therefore, in the normal observation mode, the endoscope apparatus 1A according to the present embodiment can acquire an image of the subject 101 in which hues obtained when the excitation light cut filter 22A is not provided between the subject 101 and the CCD 24 are reproduced.

Third Embodiment

Figure 13:
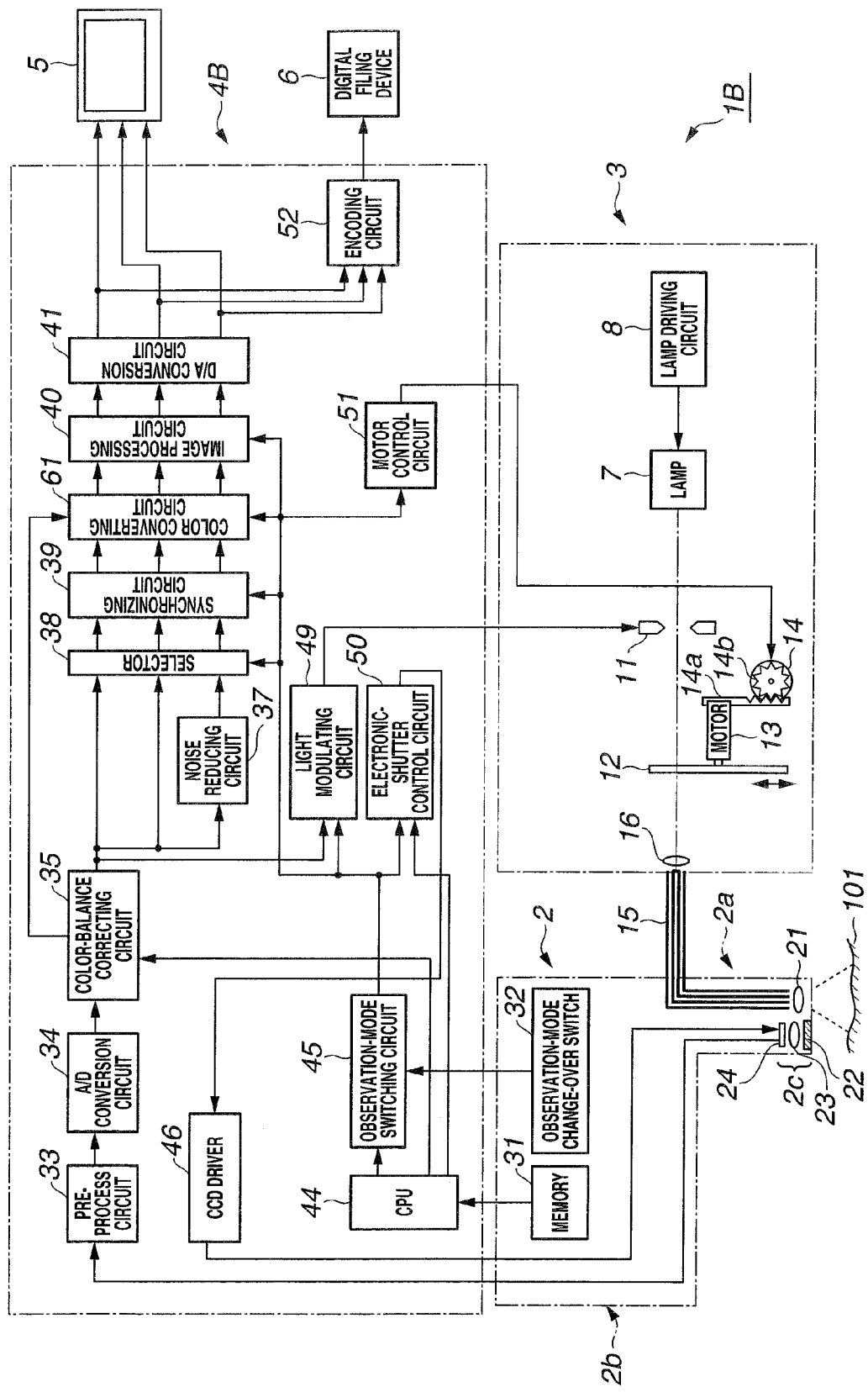
FIG. 13 is a diagram showing an example of a configuration of a main part of an endoscope apparatus according to a third embodiment of the present invention.
Figure 14:
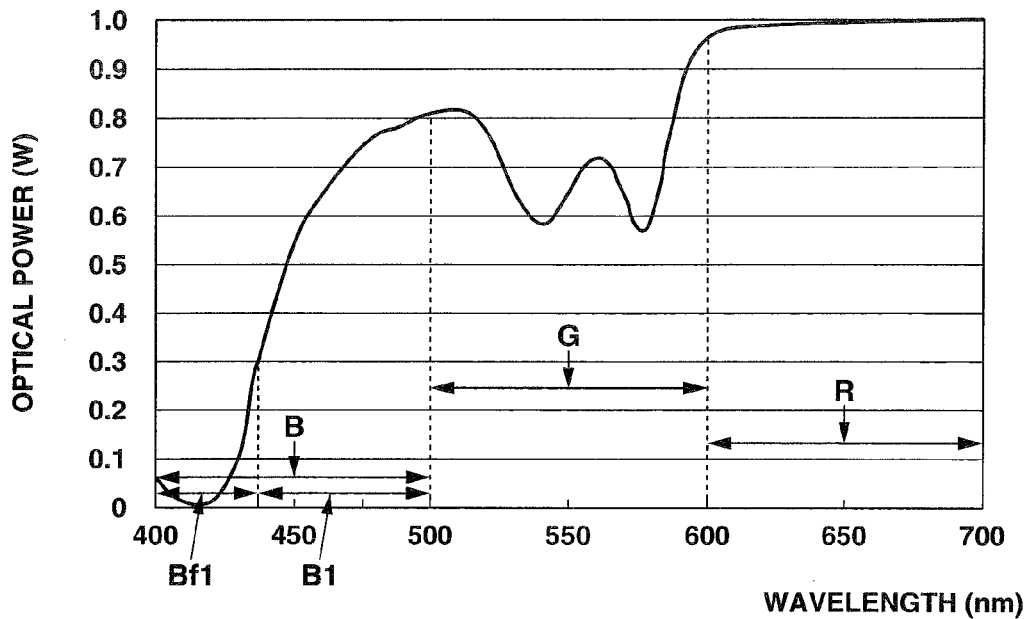
FIG. 14 is a diagram showing an optical power distribution of reflected light as light obtained when white light is irradiated on an area where capillaries accumulate and reflected from the area and a band of an excitation light cut filter shown in FIG. 13 in the optical power distribution.
Figure 15:
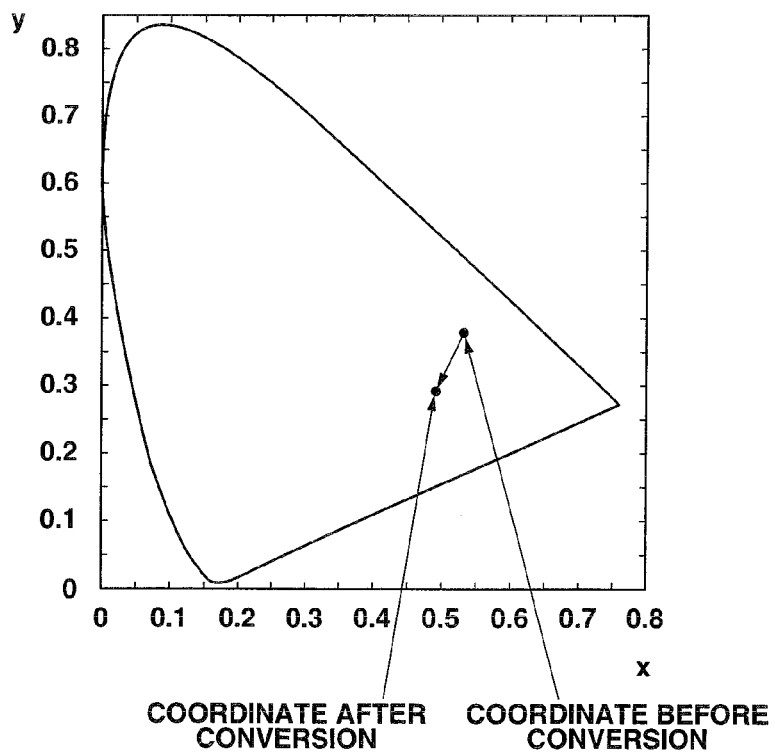
FIG. 15 is a diagram showing an example of color conversion processing performed by a color converting circuit shown in FIG. 13.
Figure 16:
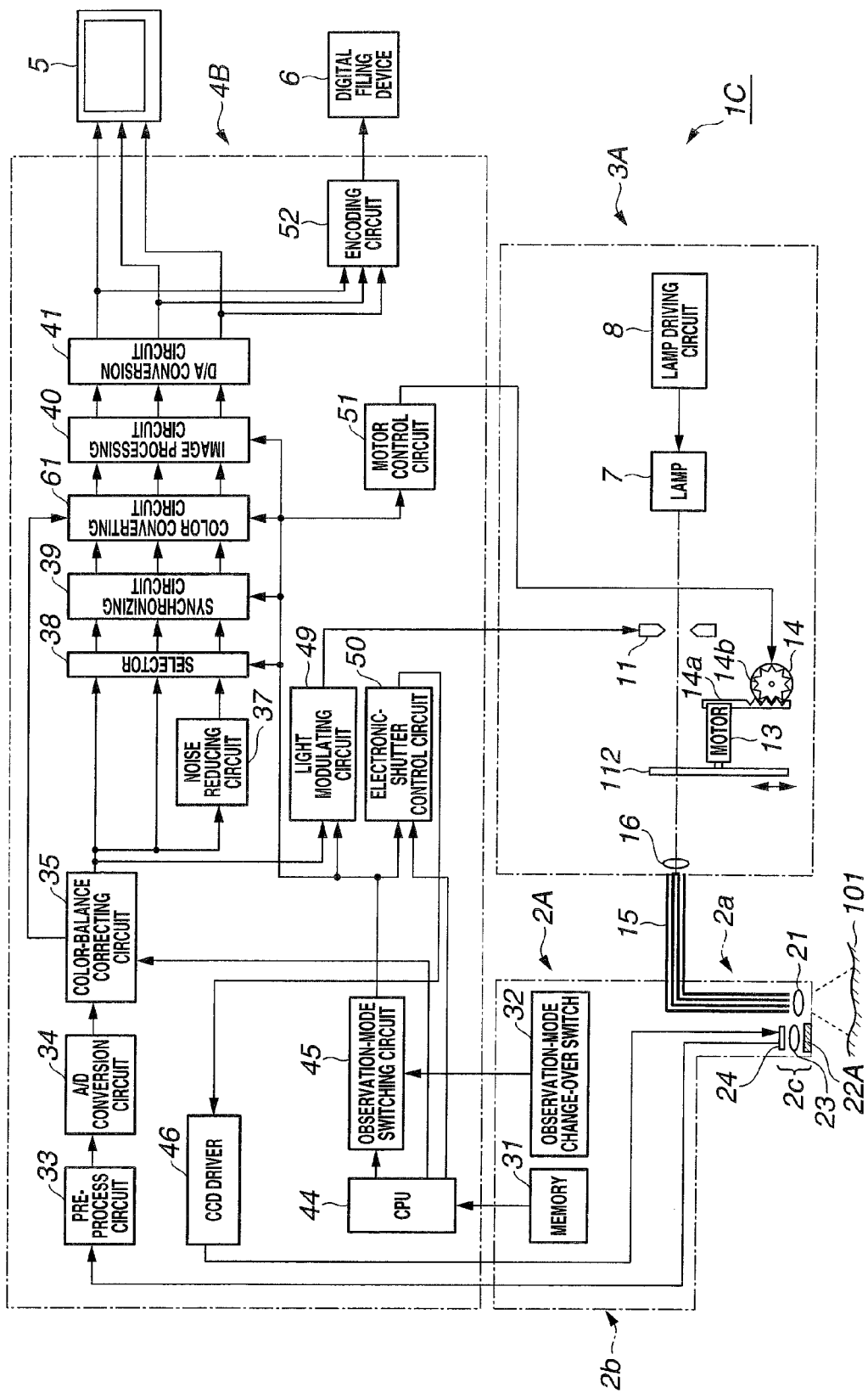
FIG. 16 is a diagram showing an example different from that shown in FIG. 13 of the configuration of the main part of the endoscope apparatus according to the third embodiment of the present invention.
Figure 17:
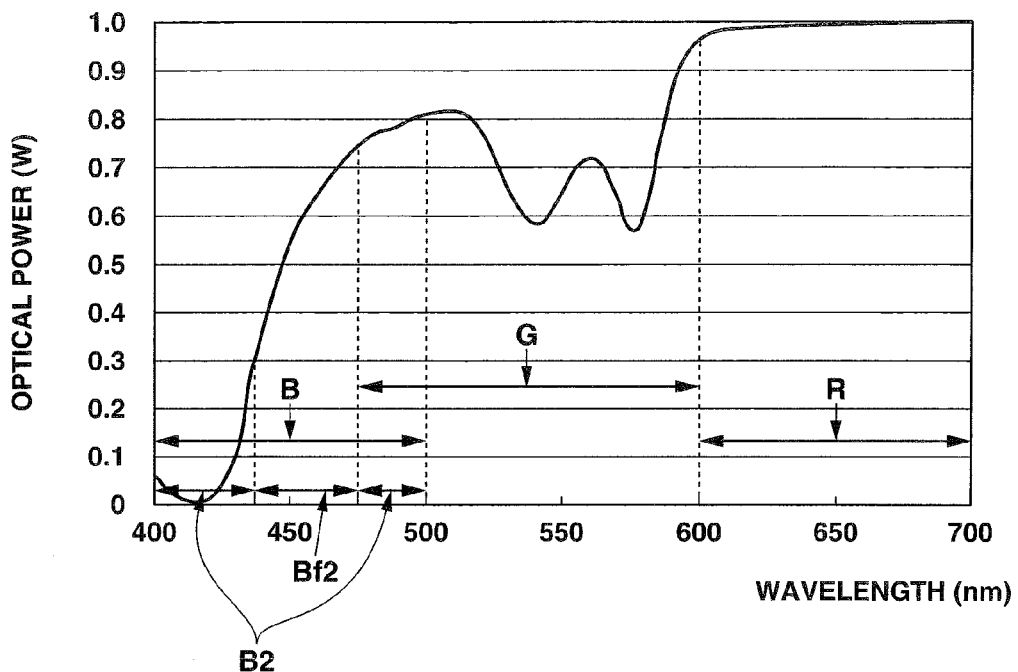
FIG. 17 is a diagram showing an optical power distribution of reflected light as light obtained when white light is irradiated on an area where capillaries accumulate and reflected from the area and a band of an excitation light cut filter shown in FIG. 16 in the optical power distribution.
Figure 18:
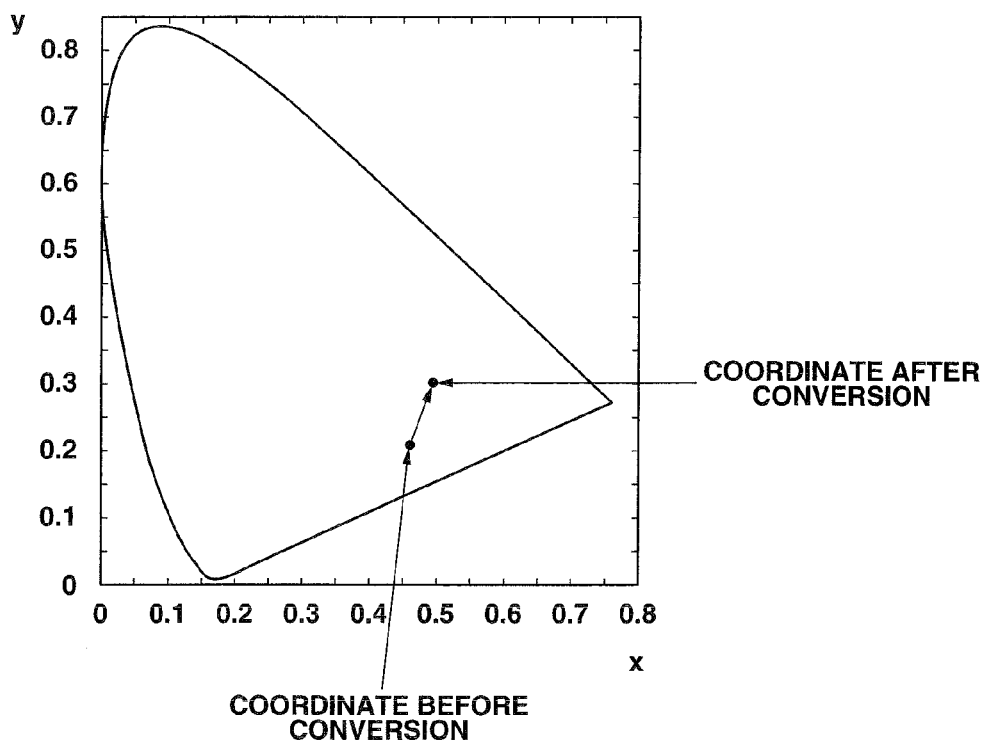
FIG. 18 is a diagram showing an example of color conversion processing performed by a color converting circuit shown in FIG. 16.

FIGS. 13 to 18 relate to a third embodiment of the present invention. FIG. 13 is a diagram showing an example of a configuration of a main part of an endoscope apparatus according to the third embodiment of the present invention. FIG. 14 is a diagram showing an optical power distribution of reflected light as light obtained when white light is irradiated on an area where capillaries accumulate and reflected from the area and a band of an excitation light cut filter shown in FIG. 13 in the optical power distribution. FIG. 15 is a diagram showing an example of color conversion processing performed by a color converting circuit shown in FIG. 13. FIG. 16 is a diagram showing an example different from that shown in FIG. 13 of the configuration of the main part of the endoscope apparatus according to the third embodiment of the present invention. FIG. 17 is a diagram showing an optical power distribution of reflected light as light obtained when white light is irradiated on an area where capillaries accumulate and reflected from the area and a band of an excitation light cut filter shown in FIG. 16 in the optical power distribution. FIG. 18 is a diagram showing an example of color conversion processing performed by a color converting circuit shown in FIG. 16.

Concerning components having the same configurations as those in the embodiments described above, detailed explanation is omitted. A configuration of the endoscope apparatus according to the present embodiment is substantially the same as the configuration of the endoscope apparatuses according to the embodiments described above. Therefore, components having configurations or actions different from those in all of the endoscope apparatuses according to the embodiments described above are mainly explained below.

In an endoscope apparatus 1B as an image generating apparatus according to the present embodiment, as shown in FIG. 13, a main part is configured to have the electronic endoscope 2, the light source device 3, a processor 4B, the monitor 5, and the digital filing device 6.

As shown in FIG. 13, the processor 4B has a configuration same as a configuration obtained by removing the contrast converting circuit 36 from the processor 4 and arranging a color converting circuit 61 at a post-stage of the synchronizing circuit 39 and a pre-stage of the image processing circuit 40 in the processor 4.

The color converting circuit 61 as a complementary processing unit applies, on the basis of color balance coefficients outputted from the color-balance correcting circuit 35 and the control by an observation-mode switching circuit 45, as complementary processing, color conversion processing described later to an image of the subject 101 corresponding to an image pickup signal from the synchronizing circuit 39 and outputs the image. The color balance coefficients are coefficients used in color balance processing by the color-balance correcting circuit 35. In the following explanation, a color balance coefficient for the R component is represented as $k_R$, a color balance coefficient for the G component is represented as $k_G$, and a color balance coefficient for the B component is represented as $k_B$. The color converting circuit 61 has a not-shown memory in which various parameters and the like for performing the color conversion processing are stored.

Next, actions of the endoscope apparatus 1B according to the present embodiment are explained.

First, a user turns on a power supply for the units of the endoscope apparatus 1B, i.e., the endoscope 2, the light source device 3, the processor 4B, the monitor 5, and the digital filing device 6 and sets the units in an activated state. It is assumed that, in the activated state, i.e., a state immediately after the power supply is turned on, the endoscope 2, the light source device 3, and the video processor 4B are set in the normal observation mode.

When the processor 4B is set in the normal observation mode, the observation-mode switching circuit 45 applies, on the basis of an instruction signal outputted from the observation-mode change-over switch 32, control for causing the units of the processor 4B to perform operation corresponding to the normal observation mode.

The motor control circuit 51 controls the motor 14 on the basis of the control by the observation-mode switching circuit 45 to thereby arrange the first filter group 12A on the emission optical path of the lamp 7. Consequently, surface-sequential illumination light of R light, G light, and B light is repeatedly emitted from the light source device 3 as illumination light corresponding to the observation mode of the processor 4B. The surface-sequential illumination light of the R light, the G light, and the B light is emitted to the subject 101 through the illumination optical system 21 after being transmitted by the light guide 15.

On the other hand, the CCD 24 operates according to a driving signal outputted from the CCD driver 46, picks up, at every predetermined timing, an image of the subject 101 sequentially illuminated by the R light, the G light, and the B light, and outputs the picked-up image of the subject 101 to the pre-process circuit 33 as an image pickup signal.

The image pickup signal outputted from the CCD 24 is outputted in a state in which the image pickup signal is subjected to pre-processing by the pre-process circuit 33, subjected to A/D conversion by the A/D conversion circuit 34, and subjected to color balance processing by the color-balance correcting circuit 35.

The light modulating circuit 49 controls a stop amount of the stop 11 on the basis of the image pickup signal from the color-balance correcting circuit 35 and the control by the observation-mode switching circuit 45 such that illumination light emitted from the light source device 3 has a light amount suitable for normal observation.

On the other hand, the R component and the G component of the image pickup signal from the color-balance correcting circuit 35 are outputted to the synchronizing circuit 39 via the selector 38. The B component of the image pickup signal from the color-balance correcting circuit 35 is outputted to the synchronizing circuit 39 via the selector 38 after being subjected to the noise reduction processing described above by the noise reducing circuit 37. The synchronizing circuit 39 outputs the inputted R component, G component, and B component to the color converting circuit 61 while synchronizing the components.

A specific example of the color conversion processing performed by the color converting circuit 61 of the processor 4B is explained.

First, the color converting circuit 61 applies the color balance coefficients $k_R$, $k_G$, and $k_B$, which are outputted from the color-balance correcting circuit 35, to Equation (1) to Equation (3) below to thereby calculate an R component value $R_b$, a G component value $G_b$, and a B component value $B_{b1}$ obtained when the excitation light cut filter 22 is taken into account.

$$R_b = A \times I(P_R) \times k_R \quad (1)$$

$$G_b = A \times I(P_G) \times k_G \quad (2)$$

$$B_{b1} = A \times I(P_{B1}) \times k_B \quad (3)$$

An optical power constant $P_R$ in Equation (1) above indicates a median calculated on the basis of an optical power distribution of a band of red as a band indicated as R in FIG. 14 among bands of reflected light as light obtained when white light is irradiated on an area where capillaries accumulate and reflected from the area.

An optical power constant $P_G$ in Equation (2) above indicates a median calculated on the basis of an optical power distribution of a band of green as a band indicated as G in FIG.

14 among bands of reflected light as light obtained when white light is irradiated on an area where capillaries accumulate and reflected from the area.

An optical power constant $P_{B1}$ in Equation (3) above indicates a median calculated on the basis of an optical power distribution of a band obtained by excluding a band cut by the excitation light cut filter 22 as a band indicated as Bf1 in FIG. 14 from the band of blue as a band indicated as B in FIG. 14, i.e., a band indicated as B1 in FIG. 14 among bands of reflected light as light obtained when white light is irradiated on an area where capillaries accumulate and reflected from the area.

An A/D conversion coefficient A in Equation (1) to Equation (3) above indicates a conversion coefficient used when the A/D conversion circuit 34 applies A/D conversion to an image pickup signal.

Photocurrent values $I(P_R)$, $I(P_G)$, and $I(P_{B1})$ in Equations (1) to (3) above are values calculated by respectively inputting the optical power constants $P_R$, $P_G$, and $P_{B1}$ as the optical power value P in Equation (4) below.

$$I(P) = (1/\eta e)(P\lambda/hc) \quad (4)$$

In Equation (4) above, $\eta$ indicates quantum efficiency, e indicates a unit charge, $\lambda$ indicates a wavelength that gives the optical power constants described above, h indicates Planck's constant, and c indicates speed of light. Next, the color converting circuit 61 applies the color balance coefficients $k_R$, $k_G$, and $k_B$ outputted from the color-balance correcting circuit 35 and the component values $R_b$, $G_b$, and $B_{b1}$ calculated by using Equation (1) to Equation (3) above to Equations (5) and (6) below to thereby convert the component values into coordinate values $X_c$ and $Y_c$ in an xy coordinate space.

$$X_c = 0.6 R_b - 0.28 G_b - 0.32 B_{b1} \quad (5)$$

$$Y_c = 0.2 R_b - 0.52 G_b + 0.31 B_{b1} \quad (6)$$

On the other hand, when a median calculated on the basis of an optical power distribution of a band of blue as a band indicated as B in FIG. 14 among bands of reflected light as light obtained when white light is irradiated on an area where capillaries accumulate and reflected from the area is set as an optical power constant $P_B$, the color converting circuit 61 applies the optical power constant $P_B$ to Equation (7) below to thereby calculate a B component value Bb obtained when the excitation light cut filter 22 is not taken into account.

$$B_b = A \times I(P_B) \times k_B \quad (7)$$

A photocurrent value $I(P_B)$ in Equation (7) above is a value calculated by substituting the optical power constant $P_B$ described above as the optical power value P in Equation (4) above.

The color converting circuit 61 applies the color balance coefficients $k_R$, $k_G$, and $k_B$ outputted from the color-balance correcting circuit 35 and the component values $R_b$, $G_b$, and $B_b$ calculated by using Equation (1), Equation (2), and Equation (7) above to Equations (8) and (9) below to thereby convert the component values into coordinate values $X_0$ and $Y_0$ in the xy coordinate space.

$$X_0 = 0.6 R_b - 0.28 G_b - 0.32 B_b \quad (8)$$

$$Y_0 = 0.2 R_b - 0.52 G_b + 0.31 B_b \quad (9)$$

Further, the color converting circuit 61 applies the color balance coefficients $k_R$, $k_G$, and $k_B$ outputted from the color-balance correcting circuit 35 and the optical power constants $P_R$, $P_G$, and $P_{B1}$ described above to Equations (10) and (11) below to thereby calculate coordinate values $X_\sigma$ and $Y_\sigma$ in the xy coordinate space.

$$X_\sigma = 0.6 \times [A \times I(P_R + \sigma_R) \times k_R] - \quad (10)$$
$$0.28 \times [A \times I(P_G + \sigma_G) \times k_G] - 0.32 \times [A \times I(P_{B1} + \sigma_{B1}) \times k_B]$$

$$Y_\sigma = 0.2 \times [A \times I(P_R + \sigma_R) \times k_R] - \quad (11)$$
$$0.52 \times [A \times I(P_G + \sigma_G) \times k_G] + 0.31 \times [A \times I(P_{B1} + \sigma_{B1}) \times k_B]$$

A standard deviation $\sigma_R$ in Equations (10) and (11) above is calculated on the basis of an optical power distribution of a band of red as a band indicated as R in FIG. 14 among bands of reflected light as light obtained when white light is irradiated on an area where capillaries accumulate and reflected from the area. A standard deviation $\sigma_G$ in Equations (10) and (11) above is calculated on the basis of an optical power distribution of a band of green as a band indicated as G in FIG. 14 among bands of reflected light as light obtained when white light is irradiated on an area where capillaries accumulate and reflected from the area. A standard deviation $\sigma_{B1}$ in Equations (10) and (11) above is calculated on the basis of an optical power distribution of a band obtained by excluding a band cut by the excitation light cut filter 22 as a band indicated as Bf1 in FIG. 14 from the band of blue as a band indicated as B in FIG. 14, i.e., a band indicated as B1 in FIG. 14 among bands of reflected light as light obtained when white light is irradiated on an area where capillaries accumulate and reflected from the area.

Photocurrent values $I(P_R+\sigma_R)$, $I(P_G+\sigma_G)$, and $I(P_{B1}+\sigma_{B1})$ in Equations (10) and (11) above are calculated by substituting values of $(P_R+\sigma_R)$, $(P_G+\sigma_G)$, and $(P_{B1}+\sigma_{B1})$ as the optical power value P in Equation (4) above.

Thereafter, the color converting circuit 61 performs color gamut determination in the xy coordinate space using Equations (12) and (13) below.

$$(X_0 - X_c) + (Y_0 - Y_c) \leq (X_c - X_\sigma)^2 + (Y_c - Y_\sigma)^2 \quad (12)$$

$$(X_0 - X_c) + (Y_0 - Y_c) > (X_c - X_\sigma)^2 + (Y_c - Y_\sigma)^2 \quad (13)$$

When the coordinate values $X_0$, $X_c$, $X_\sigma$, $Y_0$, $Y_c$, and $Y_\sigma$ satisfy the relation of Equation (12) above, the color converting circuit 61 performs processing for an inputted image pickup signal while using Equations (14) and (15) described below.

When the coordinate values $X_0$, $X_c$, $X_\sigma$, $Y_0$, $Y_c$, and $Y_\sigma$ satisfy the relation of Equation (13) above, the color converting circuit 61 outputs an inputted image pickup signal while putting through the image pickup signal without applying the following processing to the inputted image pickup signal.

When the color converting circuit 61 detects that the coordinate values $X_0$, $X_c$, $X_\sigma$, $Y_0$, $Y_c$, and $Y_\sigma$ satisfy the relation of Equation (12) above, the color converting circuit 61 applies an R component value $R_i$, a G component value $G_i$, and a B component value $B_i$ of an inputted image pickup signal to Equations (14) and (15) below to thereby convert the component values into coordinate values $X_i$ and $Y_i$ in the xy coordinate space.

$$X_i = 0.6 R_i - 0.28 G_i - 0.32 B_i \quad (14)$$

$$Y_i = 0.2 R_i - 0.52 G_i + 0.31 B_i \quad (15)$$

The color converting circuit 61 converts the coordinate values $X_i$ and $Y_i$ into coordinate values $X_e$ and $Y_e$ using Equations (16) and (17) below.

$$X_e = X_i + X_c \quad (16)$$

$$Y_e = Y_i + Y_c \quad (17)$$

Thereafter, the color converting circuit 61 calculates, on the basis of the coordinate values $X_e$ and $Y_e$, an R component value $R_e$, a G component value $G_e$, and a B component value $B_e$ after color conversion processing using Equations (18), (19), and (20) below and outputs the calculated component values to the image processing circuit 40.

$$R_e = 1.43 X_e - 0.8 Y_e + 2.0(1 - X_e - Y_e) \quad (18)$$

$$G_e = 0.18 X_e + 0.02 Y_e - 0.57(1 - X_e - Y_e) \quad (19)$$

$$B_e = -0.61 X_e - 1.5 Y_e + 3.3(1 - X_e - Y_e) \quad (20)$$

In the configuration of the endoscope apparatus 1B, the B component inputted to the color converting circuit 61 is a component, a band on a short wavelength side of which is cut by the excitation light cut filter 22. Therefore, for example, when capillaries of a surface layer of a living tissue are included in the subject 101, contrast between a portion with a large hemoglobin amount (a portion of the capillaries) and a portion with a small hemoglobin amount (a portion other than the capillaries) is reduced. Consequently, in particular, in an area where capillaries accumulate in the subject 101, an image with a strong hue of red is outputted as an image of the capillaries. In view of the point described above, the color converting circuit 61 of the endoscope apparatus 1B can apply, as the color conversion processing, for example, coordinate conversion shown in FIG. 15 to pixels present in a predetermined area in a color space to thereby output an image of capillaries with a strong hue of red as an image having an original hue while reproducing the image.

The R component $R_e$, the G component $G_e$, and the B component $B_e$ outputted from the color converting circuit 61 are outputted to the monitor 5 after being subjected to image processing by the image processing circuit 40 and subjected to D/A conversion by the D/A conversion circuit 41.

When the processing and the like described above are performed in the processor 4B, an image of the subject 101 in which hues obtained when the endoscope 2 does not have the excitation light cut filter 22 are reproduced is displayed on the monitor 5 as an image.

The user operates the observation-mode change-over switch 32 to thereby switch the observation mode of the endoscope apparatus 1B from the normal observation mode to the fluorescent observation mode.

When the processor 4B is set in the fluorescent observation mode, the observation-mode switching circuit 45 applies, on the basis of an instruction signal outputted from the observation-mode change-over switch 32, control for causing the units of the processor 4B to perform operation corresponding to the fluorescent observation mode.

The motor control circuit 51 controls the motor 14 on the basis of the control by the observation-mode switching circuit 45 to thereby arrange the second filter group 12B on the emission optical path of the lamp 7. Consequently, surface-sequential illumination light of Bn1 light and Gn light is repeatedly emitted from the light source device 3 as illumination light corresponding to the observation mode of the processor 4B. The surface-sequential illumination light of the Bn1 light and the Gn light is emitted to the subject 101 through the illumination light optical system 21 after being transmitted by the light guide 15.

On the other hand, the CCD 24 operates according to a driving signal outputted from the CCD driver 46, picks up, at every predetermined timing, an image of the subject 101 sequentially illuminated by the Bn1 light and the Gn light, and outputs the picked-up image of the subject 101 to the pre-process circuit 33 as an image pickup signal.

The image pickup signal outputted from the CCD 24 is outputted in a state in which the image pickup signal is subjected to pre-processing by the pre-process circuit 33, subjected to A/D conversion by the A/D conversion circuit 34, and subjected to color balance processing by the color-balance correcting circuit 35.

The light modulating circuit 49 controls a stop amount of the stop 11 on the basis of the image pickup signal from the color-balance correcting circuit 35 and the control by the observation-mode switching circuit 45 such that illumination light emitted from the light source device 3 has a light amount suitable for fluorescent observation.

On the other hand, the R component and the G component of the image pickup signal from the color-balance correcting circuit 35 are outputted to the synchronizing circuit 39 via the selector 38. The B component of the image pickup signal from the color-balance correcting circuit 35 is outputted to the synchronizing circuit 39 via the selector 38 after being outputted passing through the noise reducing circuit 37 (without being subjected to the noise reduction processing described above by the noise reducing circuit 37). The synchronizing circuit 39 outputs the inputted R component, G component, and B component to the color converting circuit 61 while synchronizing the components.

In the fluorescent observation mode, the color converting circuit 61 outputs the inputted image pickup signal to the image processing circuit 40 while putting through the image pickup signal.

Thereafter, the image pickup signal outputted from the color converting circuit 61 is outputted to the monitor 5 after being subjected to image processing by the image processing circuit 40 and subjected to D/A conversion by the D/A conversion circuit 41. Consequently, an image of fluorescent light emitted by the subject 101 is displayed on the monitor 5 as an image.

The color conversion processing described above is also applicable in a configuration in which a long wavelength side of the B component is cut in the normal observation mode, i.e., a configuration of an endoscope apparatus 1C shown in FIG. 16.

In the endoscope apparatus 1C, as shown in FIG. 16, a main part is configured to have the endoscope 2A, the light source device 3A, the processor 4B, the monitor 5, and the digital filing device 6. Actions of the endoscope apparatus 1C are explained.

First, the user turns on a power supply for the units of the endoscope apparatus 1C, i.e., the endoscope 2A, the light source device 3A, the processor 4B, the monitor 5, and the digital filing device 6 and sets the units in an activated state. It is assumed that, in the activated state, i.e., a state immediately after the power supply is turned on, the endoscope 2A, the light source device 3A, and the video processor 4B are set in the normal observation mode.

When the processor 4B is set in the normal observation mode, the observation-mode switching circuit 45 applies, on the basis of an instruction signal outputted from the observation-mode change-over switch 32, control for causing the units of the processor 4B to perform operation corresponding to the normal observation mode.

The motor control circuit 51 controls the motor 14 on the basis of the control by the observation-mode switching circuit 45 to thereby arrange the first filter group 12A on the emission optical path of the lamp 7. Consequently, surface-sequential illumination light of R light, G light, and B light is repeatedly emitted from the light source device 3 as illumination light corresponding to the observation mode of the processor 4B. The surface-sequential illumination light of the R light, the G light, and the B light is emitted to the subject 101 through the illumination optical system 21 after being transmitted by the light guide 15.

On the other hand, the CCD 24 operates according to a driving signal outputted from the CCD driver 46, picks up, at every predetermined timing, an image of the subject 101 sequentially illuminated by the R light, the G light, and the B light, and outputs the picked-up image of the subject 101 to the pre-process circuit 33 as an image pickup signal.

The image pickup signal outputted from the CCD 24 is outputted in a state in which the image pickup signal is subjected to pre-processing by the pre-process circuit 33, subjected to A/D conversion by the A/D conversion circuit 34, and subjected to color balance processing by the color-balance correcting circuit 35.

The light modulating circuit 49 controls a stop amount of the stop 11 on the basis of the image pickup signal from the color-balance correcting circuit 35 and the control by the observation-mode switching circuit 45 such that illumination light emitted from the light source device 3 has a light amount suitable for normal observation.

On the other hand, the R component and the G component of the image pickup signal from the color-balance correcting circuit 35 are outputted to the synchronizing circuit 39 via the selector 38. The B component of the image pickup signal from the color-balance correcting circuit 35 is outputted to the synchronizing circuit 39 via the selector 38 after the noise reduction processing is applied thereto by the noise reducing circuit 37. The synchronizing circuit 39 outputs the inputted R component, G component, and B component to the color converting circuit 61 while synchronizing the components.

The color converting circuit 61 applies the color conversion processing to the components of the inputted image pickup signal and outputs the components after the color conversion processing to the image processing circuit 40.

Specifically, the color converting circuit 61 performs the series of processing while replacing, in the equations described above, the optical power constant $P_{B1}$, the standard deviation $\sigma_{B1}$, and the color component value $B_{b1}$ with an optical power constant $P_{B2}$ described later, a standard deviation $\sigma_{b2}$ described later, and a color component value $B_{b2}$, respectively, to thereby apply the color conversion processing to the components of the inputted image pickup signal.

The optical power constant $P_{B2}$ indicates a median calculated on the basis of an optical power distribution of a band obtained by excluding a band cut by the excitation light cut filter 22A as a band indicated as Bf2 in FIG. 17 from a band of blue as a band indicated as B in FIG. 17, i.e., a band indicated as B2 in FIG. 17 among bands of reflected light as light obtained when white light is irradiated on an area where capillaries accumulate and reflected from the area.

The standard deviation $\sigma_{B2}$ is calculated on the basis of the optical power distribution of the band obtained by excluding the band cut by the excitation light cut filter 22A as the band indicated as Bf2 in FIG. 17 from the band of blue as the band indicated as B in FIG. 17, i.e., the band indicated as B2 in FIG. 17 among bands of reflected light as light obtained when white light is irradiated on an area where capillaries accumulate and reflected from the area.

In the configuration of the endoscope apparatus 1C, the B component inputted to the color converting circuit 61 is a component, a band on a long wavelength side of which is cut by the excitation light cut filter 22A. Therefore, for example, when capillaries of a surface layer of a living tissue are included in the subject 101, contrast between a portion with a large hemoglobin amount (a portion of the capillaries) and a portion with a small hemoglobin amount (a portion other than the capillaries) is reduced. Consequently, in particular, in an area where capillaries accumulate in the subject 101, an image with a weak hue of red is outputted as an image of the capillaries.

In view of the point described above, the color converting circuit 61 of the endoscope apparatus 1C can apply, as the color conversion processing, for example, coordinate conversion shown in FIG. 18 to pixels present in a predetermined area in a color space to thereby output an image of capillaries with a weak hue of red as an image having an original hue while reproducing the image.

The R component, the G component, and the B component outputted from the color converting circuit 61 are outputted to the monitor 5 after being subjected to image processing by the image processing circuit 40 and subjected to D/A conversion by the D/a conversion circuit 41.

When the processing and the like described above are performed in the processor 4B, an image of the subject 101 in which hues obtained when the endoscope 2A does not have the excitation light cut filter 22A are reproduced is displayed on the monitor 5 as an image.

Processing, operation, and the like performed by the units of the endoscope apparatus 1C in the fluorescent observation mode are the same as the processing, the operation, and the like performed by the units of the endoscope apparatus 1B. Therefore, explanation of the processing, the operation, and the like is omitted here.

As explained above, in the endoscope apparatus 1B (the endoscope apparatus 1C) according to the present embodiment, in the normal observation mode, the processing for complementing a hue of a band cut by the excitation light cut filter 22 (the excitation light cut filter 22A) is performed. Therefore, the endoscope apparatus 1B (the endoscope apparatus 1C) according to the present embodiment can acquire, in the normal observation mode, an image of the subject 101 in which hues obtained when the excitation light cut filter 22 (the excitation light cut filter 22A) is not provided between the subject 101 and the CCD 24 are reproduced.

Fourth Embodiment

Figure 19:
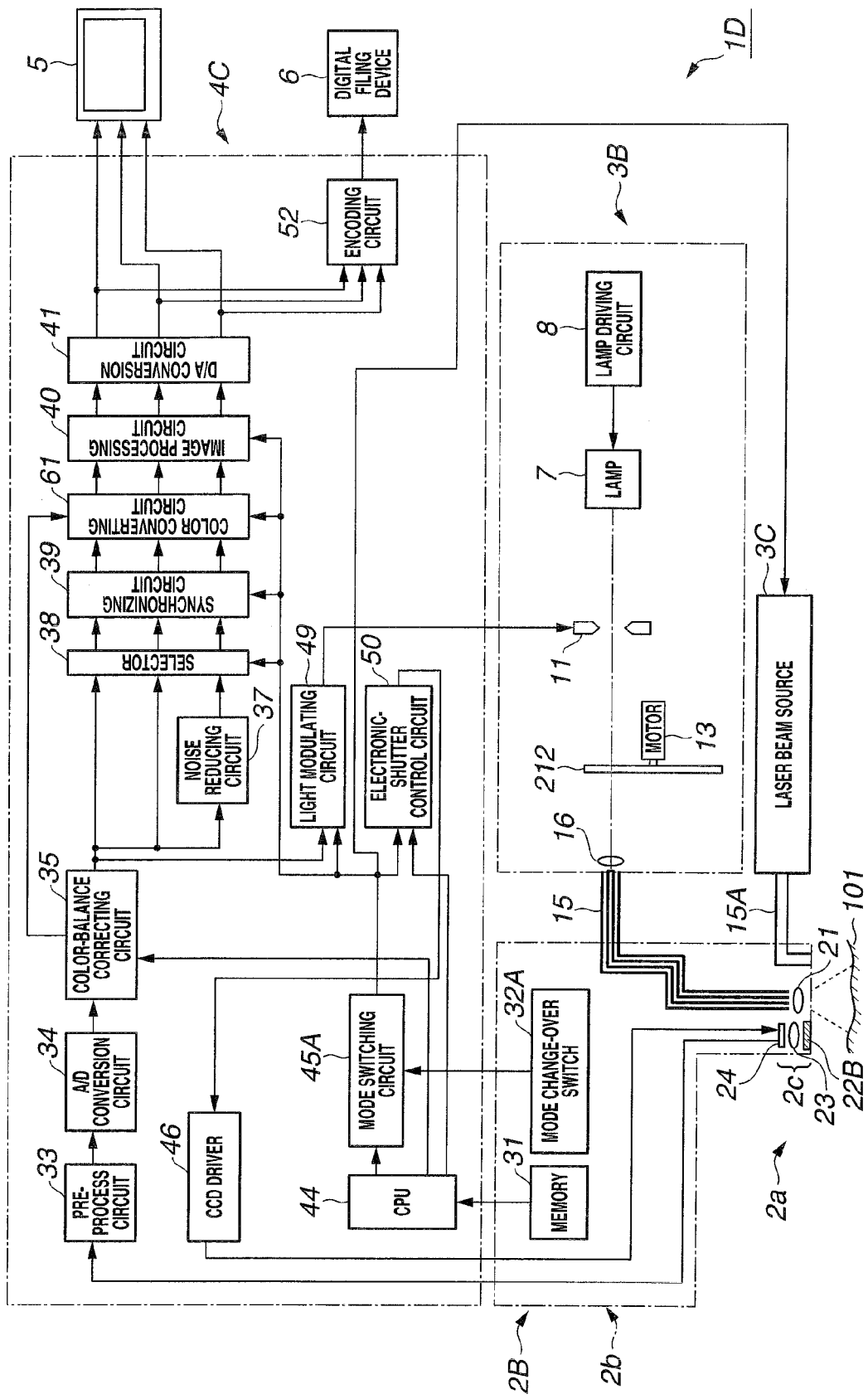
FIG. 19 is a diagram showing an example of a configuration of a main part of an endoscope apparatus according to a fourth embodiment of the present invention.
Figure 20:
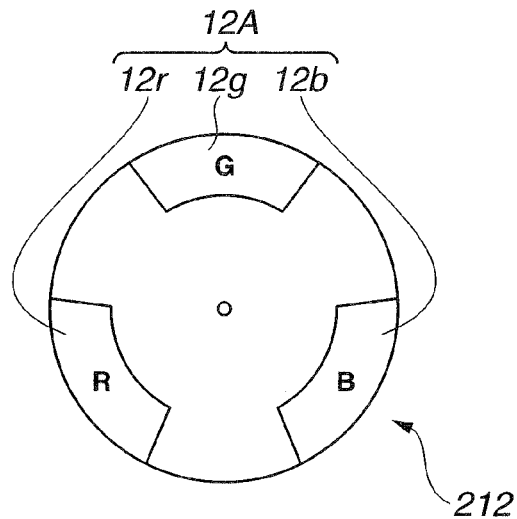
FIG. 20 is a diagram showing an example of a configuration of a rotation filter included in a light source device shown in FIG. 19.
Figure 21:
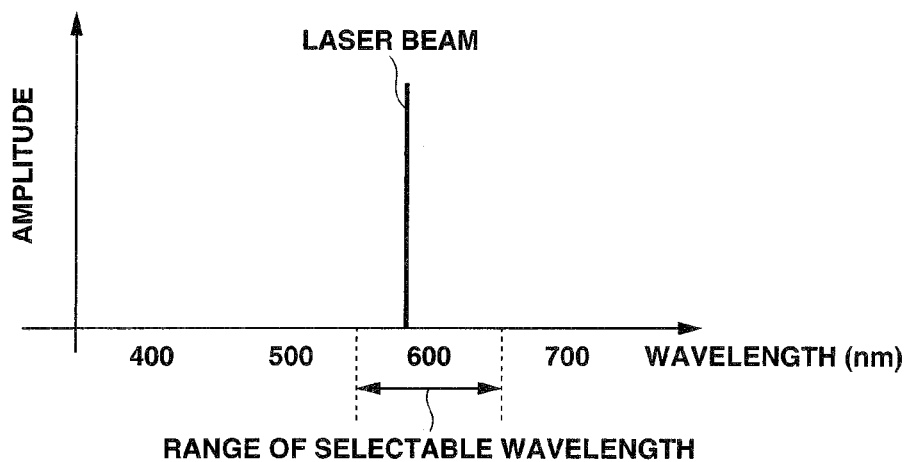
FIG. 21 is a diagram showing an example of a wavelength spectrum of a laser beam emitted in a laser beam source shown in FIG. 19.
Figure 22:
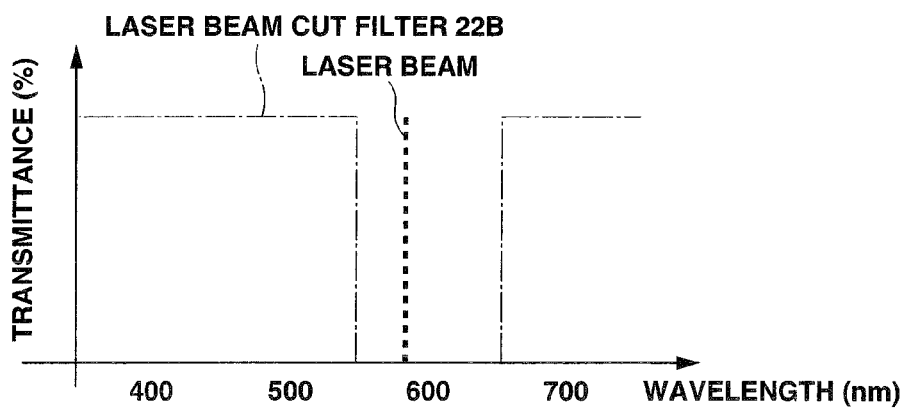
FIG. 22 is a diagram showing an example of a transmission property of a laser beam cut filter shown in FIG. 19.
Figure 23:
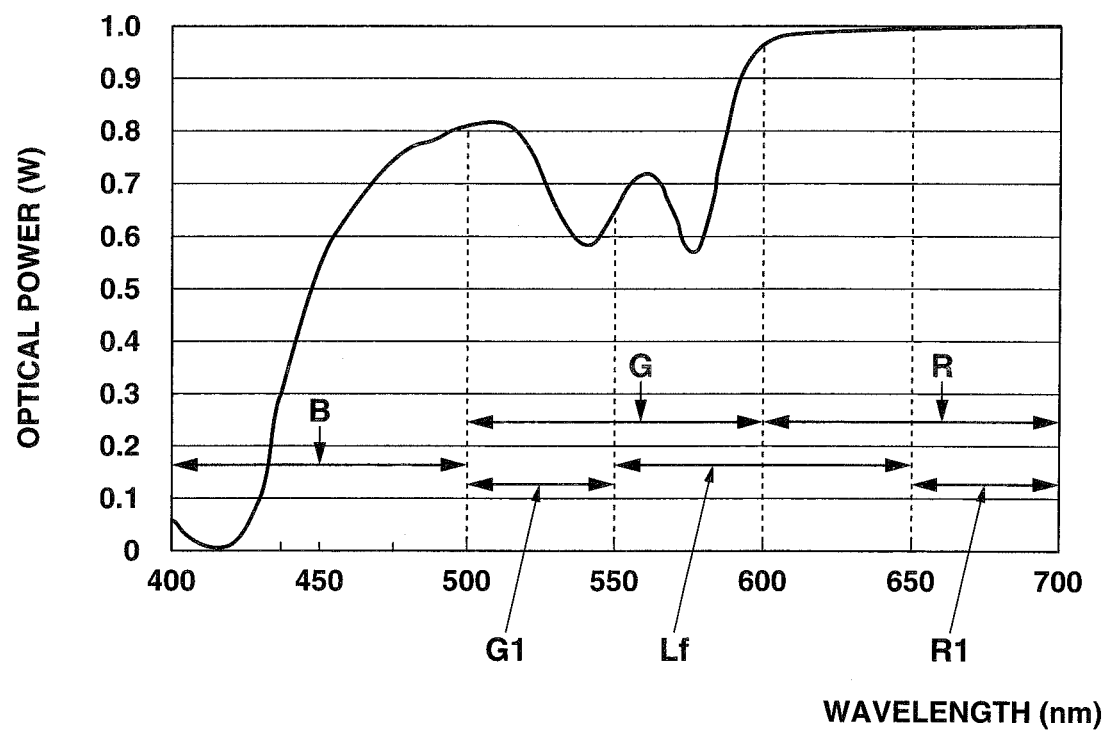
FIG. 23 is a diagram showing an optical power distribution of reflected light as light obtained when white light is irradiated on an area where capillaries accumulate and reflected from the area and a band of a laser beam cut filter shown in FIG. 19 in the optical power distribution.

FIGS. 19 to 23 relate to a fourth embodiment of the present invention. FIG. 19 is a diagram showing an example of a configuration of a main part of an endoscope apparatus according to the fourth embodiment of the present invention. FIG. 20 is a diagram showing an example of a configuration of a rotation filter included in a light source device shown in FIG. 19. FIG. 21 is a diagram showing an example of a wavelength spectrum of a laser beam emitted in a laser beam source shown in FIG. 19. FIG. 22 is a diagram showing an example of a transmission property of a laser beam cut filter shown in FIG. 19. FIG. 23 is a diagram showing an optical power distribution of reflected light as light obtained when white light is irradiated on an area where capillaries accumulate and reflected from the area and a band of a laser beam cut filter shown in FIG. 19 in the optical power distribution.

Concerning components having the same configurations as those in the embodiments described above, detailed explanation is omitted. A configuration of the endoscope apparatus according to the present embodiment is substantially the same as the configuration of the endoscope apparatuses according to the embodiments described above. Therefore, components having configurations or actions different from those in all of the endoscope apparatuses according to the embodiments described above are mainly explained below.

In an endoscope apparatus 1D as an image generating apparatus according to the present embodiment, as shown in FIG. 19, a main part is configured to have an electronic endoscope 2B, a light source device 3B, a laser beam source 3C that emits light for a photo-dynamic therapy (hereinafter abbreviated as PDT), a processor 4C, the monitor 5, and the digital filing device 6.

In an inside of an insertion section 2a in the endoscope apparatus 2B, in addition to the light guide 15, a light guide 15A that transmits light, which is supplied from the laser beam source 3C, to the distal end portion 2c of the insertion section 2a is inserted. At a rear end of the light guide 15A, a not-shown light guide connector detachably connected to the laser beam source 3C is provided. With such a configuration, the light supplied from the laser beam source 3C is emitted to the subject 101 in the living organism after being transmitted by the light guide 15A.

As shown in FIG. 19, the light source device 3B as a light source unit has a configuration same as a configuration in which the motor 14, the rack 14a, and the pinion 14b are removed from the light source device 3 and a rotation filter 212 is provided instead of the rotation filter 12 in the light source device 3.

As shown in FIG. 20, the rotation filter 212 is formed in a disc shape with a rotation axis set as a center and has the first filter group 12A including plural filters provided along a circumferential direction on an outer circumference side. In the rotation filter 212, portions other than portions where the filters of the first filter group 12A are arranged are configured by a member that blocks light. It is assumed that transmittances of the filters of the first filter group 12A in the rotation filter 212 are the same as those shown in FIG. 3.

The laser beam source 3C as a light source unit selectively supplies a laser beam having high coherence in one wavelength in, for example, a band of 550 nm to 650 nm to the light guide 15A such that it is possible to cope with various drugs given to the subject 101 in the living organism in the PDT. It is assumed that the one wavelength is a wavelength selected by a user operating a not-shown switch or the like provided in the processor 4C. An example of a wavelength spectrum of a laser beam emitted in the laser beam source 3C is shown in FIG. 21.

On the other hand, at the distal end portion 2c of the insertion section 2a, the illumination optical system 21, a laser beam cut filter 22B, the object optical system 23 that forms an image of the subject 101 transmitted through the laser beam cut filter 22B and the CCD 24 arranged in an image-forming position of the object optical system 23 are provided.

The laser beam cut filter 22B as a light cut filter section is an optical element that is arranged on a light incident side of the object optical system 23 (at a pre-stage of the CCD 24) and set such that transmittance of a wavelength band (e.g., a band of 550 nm to 650 nm) of various laser beams used for the PDT is substantially 0. In other words, the laser beam cut filter 22B has a configuration for cutting the laser beam reflected from the subject 101. An example of a transmission property of the laser beam cut filter 22B in the present embodiment is shown in FIG. 22.

In the operation section 2b of the electronic endoscope 2B, the memory 31 described in the explanation of the first embodiment in which endoscope information is stored and a mode change-over switch 32A that can output, according to operation of a user, an instruction signal for switching a mode of the endoscope apparatus 1D to a normal observation mode or a PDT mode are provided.

As shown in FIG. 19, the processor 4C has a configuration same as a configuration in which the motor control circuit 51 is removed from the processor 4B and a mode switching circuit 45A is provided instead of the observation-mode switching circuit 45 in the processor 4B.

The mode switching circuit 45A performs, on the basis of the instruction signal from the mode change-over switch 32A and the control by the CPU 44, control for switching the mode of the processor 4C to the normal observation mode or the PDT mode. The mode switching circuit 45A has a not-shown timing generator that can generate timing signals for instructing timing when a laser beam is emitted from the laser beam source 3C and timing when the units of the processor 4C perform processing or operation.

Next, actions of the endoscope apparatus 1D according to the present embodiment are explained.

First, the user turns on a power supply for the units of the endoscope apparatus 1D, i.e., the endoscope 2B, the light source device 3B, the laser beam source 3C, the processor 4C, the monitor 5, and the digital filing device 6 and sets the units in an activated state. It is assumed that, in the activated state, i.e., a state immediately after the power supply is turned on, the endoscope 2B, the light source device 3B, the laser beam source 3C, and the processor 4C are set in the normal observation mode.

When the processor 4C is set in the normal observation mode, the observation-mode switching circuit 45A applies, on the basis of an instruction signal outputted from the mode change-over switch 32A, control for causing the units of the processor 4C to perform operation corresponding to the normal observation mode. In the normal observation mode, the mode switching circuit 45A applies control for causing the laser beam source 3C to stop the emission of the laser beam to the laser beam source 3C.

Surface-sequential illumination light of R light, G light, and B light supplied from the light source device 3B are emitted to the subject 101 through the illumination optical system 21 after being transmitted by the light guide 15.

On the other hand, the CCD 24 operates according to a driving signal outputted from the CCD driver 46, picks up, at every predetermined timing, an image of the subject 101 sequentially illuminated by the R light, the G light, and the B light, and outputs the picked-up image of the subject 101 to the pre-process circuit 33 as an image pickup signal.

The image pickup signal outputted from the CCD 24 is outputted in a state in which the image pickup signal is subjected to pre-processing by the pre-process circuit 33, subjected to A/D conversion by the A/D conversion circuit 34, and subjected to color balance processing by the color-balance correcting circuit 35.

The light modulating circuit 49 controls, on the basis of the image pickup signal from the color-balance correcting circuit 35 and the control by the observation-mode switching circuit 45, a stop amount of the stop 11 such that illumination light emitted from the light source device 3B has a light amount suitable for normal observation.

On the other hand, the R component and the G component of the image pickup signal from the color-balance correcting circuit 35 are outputted to the synchronizing circuit 39 via the selector 38. The B component of the image pickup signal from the color-balance correcting circuit 35 is outputted to the synchronizing circuit 39 via the selector 38 after being subjected to the noise reduction processing by the noise reducing circuit 37. The synchronizing circuit 39 outputs the inputted R component, G component, and B component to the color converting circuit 61 while synchronizing the components.

A specific example of the color conversion processing performed by the color converting circuit 61 of the processor 4C is explained.

First, the color converting circuit 61 applies the color balance coefficients $k_R$, $k_G$, and $k_B$, which are outputted from the color-balance correcting circuit 35, to Equation (21) to Equation (23) below to thereby calculate an R component value $R_H$ obtained when the laser beam cut filter 22B is taken into account, a G component value $G_{b1}$ obtained when the laser beam cut filter 22B is taken into account, and a B component value $B_b$.

$$R_{b1} = A \times I(P_{R1}) \times k_R \quad (21)$$

$$G_{b1} = A \times I(P_{G1}) \times k_G \quad (22)$$

$$B_b = A \times I(P_B) \times k_B \quad (23)$$

An optical power constant $P_{R1}$ in Equation (21) above indicates a median calculated on the basis of an optical power distribution of a band obtained by excluding a band cut by the laser beam cut filter 22B as a band indicated as Lf in FIG. 23 from a band of red as a band indicated as R in FIG. 23, i.e., a band indicated as R1 in FIG. 23 among bands of reflected light as light obtained when white light is irradiated on an area where capillaries accumulate and reflected from the area.

An optical power constant $P_{G1}$ in Equation (22) above indicates a median calculated on the basis of an optical power distribution of a band obtained by excluding the band cut by the laser beam cut filter 22B as the band indicated as Lf in FIG. 23 from a band of green as a band indicated as G in FIG. 23, i.e., a band indicated as G1 in FIG. 23 among bands of reflected light as light obtained when white light is irradiated on an area where capillaries accumulate and reflected from the area.

Photocurrent values $I(P_{R1})$ and $I(P_{G1})$ in Equations (21) and (22) are values calculated by substituting the optical power constants $P_{R1}$ and $P_{G1}$ as the optical power value P in Equation (4).

Next, the color converting circuit 61 applies the color balance coefficients $k_R$, $k_G$, and $k_B$ outputted from the color-balance correcting circuit 35 and the component values $R_{b1}$, $G_{b1}$, and $B_b$ calculated by using Equation (21) to Equation (23) above to Equations (24) and (25) below to thereby convert the component values into coordinate values $X_c$ and $Y_c$ in an xy coordinate space.

$$X_{c1} = 0.6 R_{b1} - 0.28 B_{b1} - 0.32 B_b \quad (24)$$

$$Y_{c1} = 0.2 R_{b1} - 0.52 G_{b1} + 0.31 B_b \quad (25)$$

On the other hand, the color converting circuit 61 applies the optical power constants $P_R$ and $P_G$ described in the explanation of the third embodiment to Equations (26) and (27) below, respectively, to thereby calculate an R component value $R_b$ obtained when the laser beam cut filter 22B is not taken into account and a G component value $G_b$ obtained when the laser beam cut filter 22B is not taken into account.

$$R_b = A \times I(P_R) \times k_B \quad (26)$$

$$G_b = A \times I(P_G) \times k_R \quad (27)$$

The color converting circuit 61 applies the color balance coefficients $k_R$, $k_G$, and $k_B$ outputted from the color-balance correcting circuit 35 and the component values $R_b$, $G_b$, and $B_b$ calculated by using Equation (26) and Equation (27) above to Equations (28) and (29) below to thereby convert the component values into coordinate values $X_0$ and $Y_0$ in the xy coordinate space.

$$X_0 = 0.6 R_b - 0.28 G_b - 0.32 B_b \quad (28)$$

$$Y_0 = 0.2 R_b - 0.52 G_b + 0.31 B_b \quad (29)$$

Further, the color converting circuit 61 applies the color balance coefficients $k_R$, $k_G$, and $k_B$ outputted from the color-balance correcting circuit 35 and the optical power constants $P_{R1}$, $P_{G1}$, and $P_B$ described above to Equations (30) and (31) below to thereby calculate coordinate values $X_{o1}$ and $Y_{o1}$ in the xy coordinate space.

$$X_{o1} = 0.6 \times [A \times I(P_{R1} + \sigma_{R1}) \times k_R] - 0.28 \times [A \times I(P_{G1} + \sigma_{G1}) \times k_G] - 0.32 \times [A \times I(P_B + \sigma_B) \times k_B] \quad (30)$$

$$Y_{o1} = 0.2 \times [A \times I(P_{R1} + \sigma_{R1}) \times k_R] - 0.52 \times [A \times I(P_{G1} + \sigma_{G1}) \times k_G] + 0.31 \times [A \times I(P_B + \sigma_B) \times k_B] \quad (31)$$

A standard deviation $\sigma_{R1}$ in Equations (30) and (31) above is calculated on the basis of an optical power distribution of a band obtained by excluding a band cut by the laser beam cut filter 22B as a band indicated as Lf in FIG. 23 from a band of red as a band indicated as R in FIG. 23, i.e., a band indicated as R1 in FIG. 23 among bands of reflected light as light obtained when white light is irradiated on an area where capillaries accumulate and reflected from the area.

A standard deviation $\sigma_{G1}$ in Equations (30) and (31) above is calculated on the basis of an optical power distribution of a band obtained by excluding the band cut by the laser beam cut filter 22B as the band indicated as Lf in FIG. 23 from a band of green as a band indicated as G in FIG. 23, i.e., a band indicated as G1 in FIG. 23 among bands of reflected light as light obtained when white light is irradiated on an area where capillaries accumulate and reflected from the area.

A standard deviation $\sigma_B$ in Equations (30) and (31) above is calculated on the basis of an optical power distribution of a band of blue as a band indicated as B in FIG. 23 among bands of reflected light as light obtained when white light is irradiated on an area where capillaries accumulate and reflected from the area. Photocurrent values $I(P_{R1} + \sigma_{R1})$, $I(P_{G1} + \sigma_{G1})$, and $I(P_B + \sigma_B)$ in Equations (30) and (31) above are calculated by substituting values of $(P_{R1} + \sigma_{R1})$, $(P_{G1} \sigma_{G1})$, and $(P_B + \sigma_B)$ as the optical power value P in Equation (4) above.

Thereafter, the color converting circuit 61 performs color gamut determination in the xy coordinate space using Equations (32) and (33) below.

$$(X_0 - X_{c1}) + (Y_0 - Y_{c1}) \leq (X_{c1} - C_{o1})^2 + (Y_{c1} - Y_{o1})^2 \quad (32)$$

$$(X_0 - X_{c1}) + (Y_0 - Y_{c1}) > (X_{c1} - C_{o1})^2 + (Y_{c1} - Y_{o1})^2 \quad (33)$$

When the coordinate values $X_0$, $X_{c1}$, $X_{o1}$, $Y_0$, $Y_{c1}$, and $Y_{o1}$ satisfy the relation of Equation (32) above, the color converting circuit 61 performs processing for an inputted image pickup signal while using Equations (34) and (35) described below. When the coordinate values $X_0$, $X_{c1}$, $X_{o1}$, $Y_0$, $Y_{c1}$, and $Y_{o1}$ satisfy the relation of Equation (33) above, the color converting circuit 61 outputs an inputted image pickup signal while putting through the image pickup signal without applying the following processing to the inputted image pickup signal.

When the color converting circuit 61 detects that the coordinate values $X_0$, $X_{c1}$, $X_{o1}$, $Y_0$, $Y_{c1}$, and $Y_{o1}$ satisfy the relation of Equation (32) above, the color converting circuit 61 applies an R component value $R_{i1}$ a G component value $G_{i1}$, and a B component value $B_{i1}$ of an inputted image pickup signal to Equations (34) and (35) below to thereby convert the component values into coordinate values $X_{i1}$ and $Y_{i1}$ in the xy coordinate space.

$$X_{i1} = 0.6 R_{i1} - 0.28 G_{i1} - 0.32 B_{i1} \quad (34)$$

$$Y_{i1} = 0.2 R_{i1} - 0.52 G_{i1} + 0.31 B_{i1} \quad (35)$$

The color converting circuit 61 converts the coordinate values $X_{i1}$ and $Y_{i1}$ into coordinate values $X_{e1}$ and $Y_{e1}$ using Equations (36) and (37) below.

$$X_{e1} = X_{i1} + X_{c1} \tag{36}$$

$$Y_{e1} = Y_{i1} + Y_{c1} \tag{37}$$

Thereafter, the color converting circuit 61 calculates, on the basis of the coordinate values $X_{e1}$ and $Y_{e1}$, an R component value $R_{e1}$, a G component value $G_{e1}$, and a B component value $B_{e1}$ after color conversion processing using Equations (38), (39), and (40) below and outputs the calculated component values to the image processing circuit 40.

$$R_{e1} = 1.43 X_{e1} - 0.8 Y_{e1} + 2.0(1 - X_{e1} - Y_{e1}) \tag{38}$$

$$G_{e1} = 0.18 X_{e1} - 0.02 Y_{e1} + 0.57(1 - X_{e1} - Y_{e1}) \tag{39}$$

$$B_{e1} = -0.61 X_{e1} - 1.5 Y_{e1} + 3.3(1 - X_{e1} - Y_{e1}) \tag{40}$$

In the configuration of the endoscope apparatus 1D, the R component inputted to the color converting circuit 61 is a component, a band on a short wavelength side of which is cut by the laser beam cut filter 22B. In the configuration of the endoscope apparatus 1D, the G component inputted to the color converting circuit 61 is a component, a band on a long wavelength side of which is cut by the laser beam cut filter 22B. Therefore, for example, when capillaries of a surface layer of a living tissue are included in the subject 101, contrast between a portion with a large hemoglobin amount (a portion of the capillaries) and a portion with a small hemoglobin amount (a portion other than the capillaries) is reduced.

In view of the point described above, the color converting circuit 61 of the endoscope apparatus 1D can apply, as the color conversion processing, coordinate conversion for pixels present in a predetermined area in a color space to thereby output an image of capillaries as an image having an original hue while reproducing the image.

The R component $R_{e1}$, the G component $G_{e1}$, and the B component $B_{e1}$ outputted from the color converting circuit 61 are outputted to the monitor 5 after being subjected to image processing by the image processing circuit 40 and subjected to D/A conversion by the D/A conversion circuit 41.

When the processing and the like described above are performed in the processor 4C, an image of the subject 101 in which hues obtained when the endoscope 2B does not have the laser beam cut filter 22B are reproduced is displayed on the monitor 5 as an image.

The user operates the mode change-over switch 32A to thereby switch the mode of the endoscope apparatus 1D from the normal observation mode to the PDT mode. It is assumed that the user gives, before performing the switching operation, a drug for the PDT to the subject 101 in the living organism and performs setting such that a laser beam coherent in one wavelength corresponding to the drug is emitted from the laser beam source 3C.

When the processor 4C is set in the PDT mode, the mode switching circuit 45A applies, on the basis of an instruction signal outputted from the mode change-over switch 32A, control for causing the units of the processor 4C to perform operation corresponding to the PDT mode.

The laser beam source 3C emits, on the basis of the control by the mode switching circuit 45A, the laser beam coherent in the one wavelength set in advance by the user. The laser beam is emitted from the distal end portion 2c of the endoscope 2B to the subject 101 after being transmitted by the light guide 15A.

On the other hand, the CCD 24 operates according to a driving signal outputted from the CCD driver 46, picks up, at every predetermined timing, an image of the subject 101 sequentially illuminated by the R light, the G light, and the B light, and outputs the picked-up image of the subject 101 to the pre-process circuit 33 as an image pickup signal.

The image pickup signal outputted from the CCD 24 is outputted in a state in which the image pickup signal is subjected to pre-processing by the pre-process circuit 33, subjected to A/D conversion by the A/D conversion circuit 34, and subjected to color balance processing by the color-balance correcting circuit 35.

The light modulating circuit 49 controls a stop amount of the stop 11 on the basis of the image pickup signal from the color-balance correcting circuit 35 and the control by the observation-mode switching circuit 45A such that illumination light emitted from the light source device 3B has a light amount suitable for the PDT.

On the other hand, the R component and the G component of the image pickup signal from the color-balance correcting circuit 35 are outputted to the synchronizing circuit 39 via the selector 38. The B component of the image pickup signal from the color-balance correcting circuit 35 is outputted to the synchronizing circuit 39 via the selector 38 after being outputted passing through the noise reducing circuit 37 (without being subjected to the noise reduction processing by the noise reducing circuit 37). The synchronizing circuit 39 outputs the inputted R component, G component, and B component to the color converting circuit 61 while synchronizing the components.

In the PDT mode, the color converting circuit 61 outputs the inputted image pickup signal to the image processing circuit 40 while putting through the image pickup signal.

Thereafter, the image pickup signal outputted from the color converting circuit 61 is outputted to the monitor 5 after being subjected to image processing by the image processing circuit 40 and subjected to D/A conversion by the D/A converting circuit 41. Consequently, an image of the subject 101 in the PDT mode is displayed on the monitor 5 as an image.

As described above, in the endoscope apparatus 1D according to the present embodiment, in the normal observation mode, the processing for complementing hues of a band cut by the laser beam cut filter 22B is performed. Therefore, in the normal observation mode, the endoscope apparatus 1D according to the present embodiment can acquire an image of the subject 101 in which hues obtained when the laser beam cut filter 22B is not provided between the subject 101 and the CCD 24 are reproduced.

The present invention is not limited to the embodiments described above. It goes without saying that various alterations and applications are possible in a range not departing from the spirit of the present invention.

What is claimed is:

1. An image generating apparatus comprising:
    a first light source unit that emits, as illumination light for illuminating a subject, light in a first wavelength band to the subject;
    a second light source unit that emits light in a second wavelength band, which is a part of the first wavelength band, to the subject;
    an image pickup unit that picks up an image of the subject and outputs the image as an image pickup signal;
    a light cut filter unit that is provided between the subject and the image pickup unit and cuts light in the second wavelength band reflected from the subject; and
    a complementary processing unit that applies, on the basis of the image pickup signal, complementary processing to a component corresponding to the second wavelength band cut by the light cut filter unit in the image of the subject picked up by the image pickup unit in a state in which the subject is illuminated by the light in the first wavelength band, wherein the complementary processing unit performs, as the complementary processing, one of processing for reducing a black level in a luminance of the component corresponding to the second wavelength band, processing for eliminating a high frequency component in the component corresponding to the second wavelength band in one of two portions of the subject, and processing for correcting strength of hues between the two portions of the subject in accordance with the calculation results of optical power values of reflected light, which is generated when the light in the first wavelength band is irradiated to a predetermined living body structure, in a case where the reflected light passes through the light cut filter unit and in a case where the reflected light do not pass through the light cut filter unit.

2. The image generating apparatus according to claim 1, further comprising a noise-reduction processing unit that performs, on the basis of the image pickup signal, noise reduction processing for reducing noise that occurs in an edge portion in an image of the subject picked up by the image pickup unit in a state in which the subject is illuminated by light in the first wavelength band.

3. The image generating apparatus according to claim 1, wherein the first wavelength band is wavelength bands for each of red, green, and blue.

4. The image generating apparatus according to claim 2, wherein the first wavelength band is wavelength bands for each of red, green, and blue.

5. The image generating apparatus according to claim 3, wherein the second wavelength band is a predetermined wavelength band in the wavelength band for blue.

6. The image generating apparatus according to claim 4, wherein the second wavelength band is a predetermined wavelength band in the wavelength band for blue.

7. The image generating apparatus according to claim 5, wherein the predetermined wavelength band is a wavelength band in which autofluorescence can be generated in a living tissue as the subject.

8. The image generating apparatus according to claim 6, wherein the predetermined wavelength band is a wavelength band in which autofluorescence can be generated in a living tissue as the subject.

9. The image generating apparatus according to claim 1, wherein the predetermined living body structure comprises capillaries.

* * * * *